United States Patent
Brown et al.

(10) Patent No.: US 9,097,672 B2
(45) Date of Patent: Aug. 4, 2015

(54) METHOD AND SYSTEM FOR DETECTING BIOLOGICAL MOLECULES IN SAMPLES

(75) Inventors: R. Stephen Brown, Kingston (CA); Eric Marcotte, Kingston (CA); Doug Wilton, Kingston (CA); Peter Gallant, Kingston (CA); David Dolphin, Inverary (CA); Lee Underwood, High Wycombe (GB)

(73) Assignees: QUEENS'S UNIVERSITY AT KINGSTON, Kingston (CA); PATHOGEN DETECTION SYSTEMS, INC., Kingston (CA)

( * ) Notice: Subject to any disclaimer, the term of this patent is extended or adjusted under 35 U.S.C. 154(b) by 0 days.

(21) Appl. No.: 13/704,719

(22) PCT Filed: Jun. 17, 2011

(86) PCT No.: PCT/CA2011/000722
§ 371 (c)(1),
(2), (4) Date: Apr. 29, 2013

(87) PCT Pub. No.: WO2011/156915
PCT Pub. Date: Dec. 22, 2011

(65) Prior Publication Data
US 2013/0217040 A1 Aug. 22, 2013

Related U.S. Application Data

(60) Provisional application No. 61/356,384, filed on Jun. 18, 2010.

(51) Int. Cl.
*G01N 21/64* (2006.01)
*G01N 33/12* (2006.01)
*G01N 33/18* (2006.01)
*B01L 3/00* (2006.01)

(52) U.S. Cl.
CPC ........ *G01N 21/6486* (2013.01); *G01N 21/6428* (2013.01); *G01N 21/6452* (2013.01); *B01L 3/50825* (2013.01); *G01N 33/12* (2013.01); *G01N 33/1826* (2013.01); *G01N 2021/6417* (2013.01); *G01N 2021/6482* (2013.01); *G01N 2021/6484* (2013.01); *G01N 2201/062* (2013.01)

(58) Field of Classification Search
None
See application file for complete search history.

(56) References Cited

U.S. PATENT DOCUMENTS

| | | |
|---|---|---|
| 4,974,929 A | 12/1990 | Curry |
| 5,238,809 A | 8/1993 | Wolfbeis |
| 5,364,767 A | 11/1994 | Flowers et al. |
| 5,376,551 A | 12/1994 | Yoshikami |
| 5,567,290 A | 10/1996 | Vadgama et al. |
| 5,861,270 A | 1/1999 | Nelis |
| 6,060,266 A | 5/2000 | Naqui et al. |
| 6,566,508 B2 | 5/2003 | Bentsen et al. |
| 6,753,186 B2 | 6/2004 | Moskoff |
| 7,096,053 B2 | 8/2006 | Loeb et al. |
| 7,402,426 B2 | 7/2008 | Brown et al. |
| 8,377,686 B2 | 2/2013 | Brown et al. |
| 2003/0222012 A1 | 12/2003 | Lee et al. |
| 2003/0228681 A1 | 12/2003 | Ritts et al. |
| 2004/0047535 A1 | 3/2004 | Ukrainczyk |

FOREIGN PATENT DOCUMENTS

| | | |
|---|---|---|
| EP | 0044140 | 1/1982 |
| EP | 1 335 200 | 8/2003 |
| GB | 2 078 370 | 1/1982 |
| JP | 57-030952 | 2/1982 |
| JP | 63-247646 | 10/1988 |
| JP | 64-63842 | 3/1989 |
| JP | 3065639 | 3/1991 |
| JP | 04-330298 | 11/1992 |
| JP | 07-151725 | 6/1995 |
| WO | 9216648 | 10/1992 |
| WO | 9303051 | 2/1993 |
| WO | 9932655 | 7/1999 |

OTHER PUBLICATIONS

Lindqvist, Christer; et al; "Flow Cytometric Analysis of Bioluminescence Emitted by Recombinant Baculovirus-Infected Insect Cells" Cytometry, 15, 207-212, 1994.*

Alonso, J.L.; et al. "Quantitative Determination of *E. coli* and Fecal Coliforms in Water Using a Chromogenic Medium". J. Envir. Sci. Health A33(6): 1229-1248 (1998).

Arkles, B. "Look What You Can Make Out of Silicones". Chemtech. 13: 542-555 (1983).

(Continued)

*Primary Examiner* — Blaine Lankford
*Assistant Examiner* — David Berke-Schlessel

(57) ABSTRACT

A system for detecting presence of an organism having an enzyme in a sample, comprising: a cartridge for containing the sample and a substrate such that the enzyme can react with the substrate to produce a biological molecule; a partitioning element mounted in a recess in a base of the cartridge, the partitioning element allowing partitioning of the biological molecule thereinto; a light source for irradiating the biological molecule partitioned into the partitioning element; and, a detector for detecting fluorescence of the biological molecule partitioned into the partitioning element, the detected fluorescence being indicative of presence of the organism in the sample; wherein the light source is in a raised cartridge mount of the system that mates with the recess in the base of the cartridge.

7 Claims, 34 Drawing Sheets

(56) References Cited

OTHER PUBLICATIONS

D'Auriac, M.B.A.; et al. "Field Evaluation of a Semiautomated Method for Rapid and Simple Analysis of Recreational Water Microbiological Quality". Applied and Environmental H / Microbiology 66:4401-4407 (2000).

Davies, C.M.; et al. "Rapid Enzymatic Detection of Faecal Pollution". Wat. Sci. Tech. 34(7-8):169-171 (1996).

Davies, C.M.; et al. "Field Evaluation of a Rapid Portable Test for Monitoring Fecal Coliforms in Coastal Waters". Environ. Texico/. 14: 355-359 (1999).

"European School on Sensors for Food Applications", Marciana Marina, Elba Island, Apr. 18-29, 1999, www.inapg.inra.fr/ens_rech/siab/asteq/elba/elba index.

Fischer, B.; et al. "A Novel Method for Stereoselective Glucuronidation". J.Org. Chem. 49:4988-4993 ( 1984 ).

Frampton, E.W.; et al. "Methods for *Escherichia coli* Identification in Food, Water and Clinical Samples Based on Beta-Glucuronidase Detection". J. Appl. Bacter. 74: 223-233 (1993).

Sansubrino et al. "Development of an optical fibre sensor for ammonia, urea, urease, and IgG." Biosensors & Bioelectronics 9 (1994) 207-216.

Gee, KR; et al. "Fiuorogenic Substrates Based on Fluorinated Umbelliferones for Continuous Assays of Phosphatases and B-Galactosidases". Anal. Biachem. 273: 41-48 (1999).

Hall, J.; et al. Reduction Products of the Hydroxyanthraquinones Part II. J. Chem. Sac. 123: 2029-2037 (1923).

Kleine, H.P.; et al. "Phase-Transfer-Catalyzed Syntheses of 2,3,4,6-tetra-0-acetyl-Beta-D-galactopyranosides". Carbo. Res. 142: 333-337 (1985).

Kiene, L.; et al. "On-line Detection of Coliforms". Water Supply. 17(2): 81-86 (1999).

Ley, A. N.; et al. "Indoxyl-Beta-D-glucuronide, a Novel Chromogenic Reagent for Specific Detection and Enumeration of *Escherichia coli* in Environmental Samples". Can. J. Microbial. 34: 690-693 (1988).

Manafi, M.; et al. "Fiuorogenic and Chromogenic Substrates Used in Bacterial Diagnostics". Microbial. Rev. 55(3): 335-348 (1991).

Marazuela, M.D.; et al. "Fiber-Optic Biosensors—An Overview". Anal. Bioanal. Chem. 372: 664-682 (2002).

Nelis, H.; et al. "Enzymatic Detection of Coliforrns and *Escherichia coli* Within 4 Hours". Water, Air, and Soil Pollution 123: 43-52 (2000).

Park, S.J. et at. "Spectrofluorometric Assay for Rapid Detection of Total and Fecal Coliforrns from Surface Water". AQPI. Enviro. Micro. 61(5): 2027-2029 (1995).

Prescott, A.; et al. "Feasibility of Fast-Response Testing for Coliform Bacteria in Distribution Systems" American Water Works Association Research Foundation, 2002.

Robertson, W .; et al. Evaluation of a Rapid Method for *E. coli* and Thermotolerant Coliforrns in Recreational Waters. Wat. Sci. Tech. 38(12): 87-90 (1998).

Stachulski, A.V.; et al. "The Synthesis of 0-glucuronides". Natural Product Reports. 173-186 (1998).

\* cited by examiner

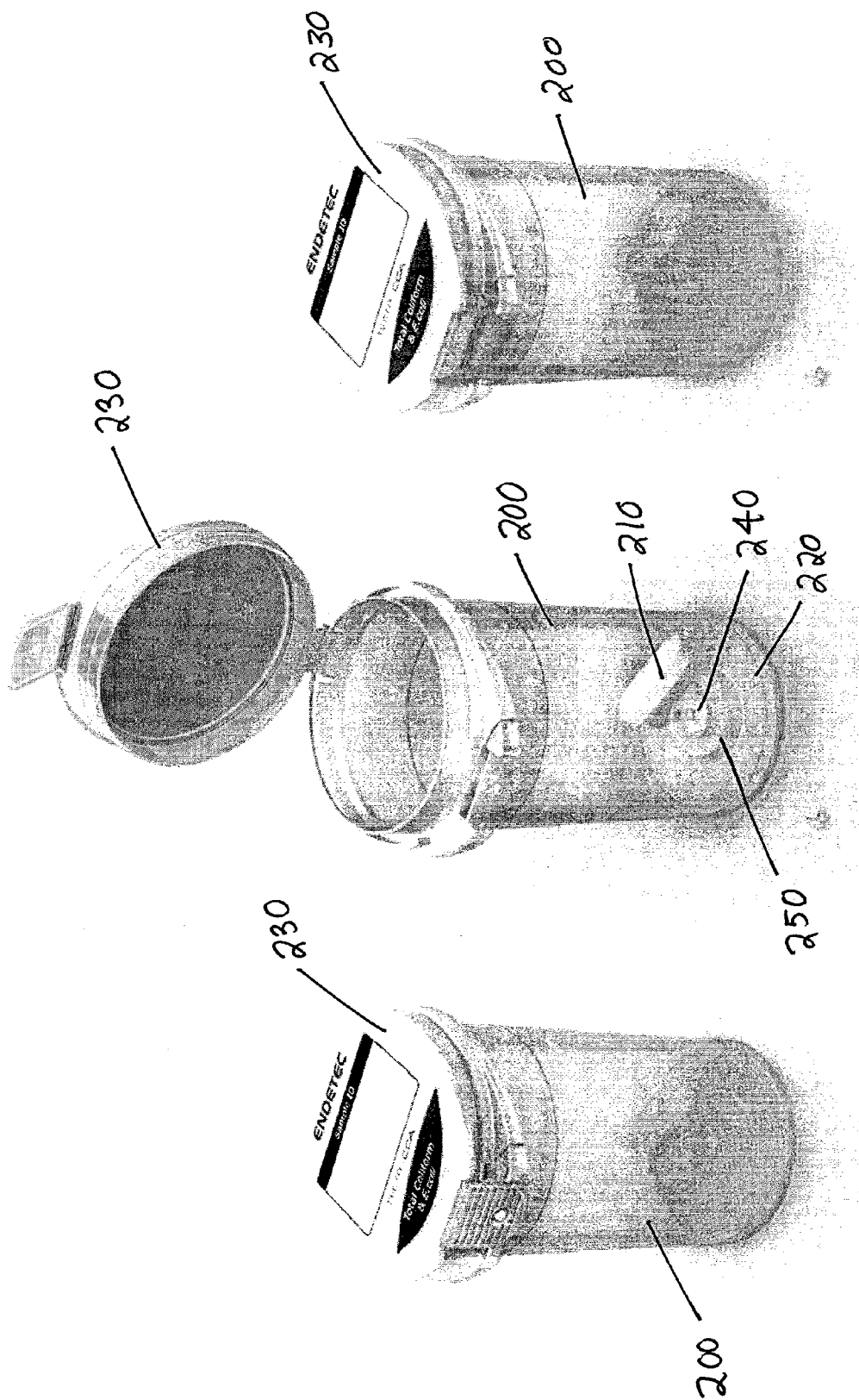

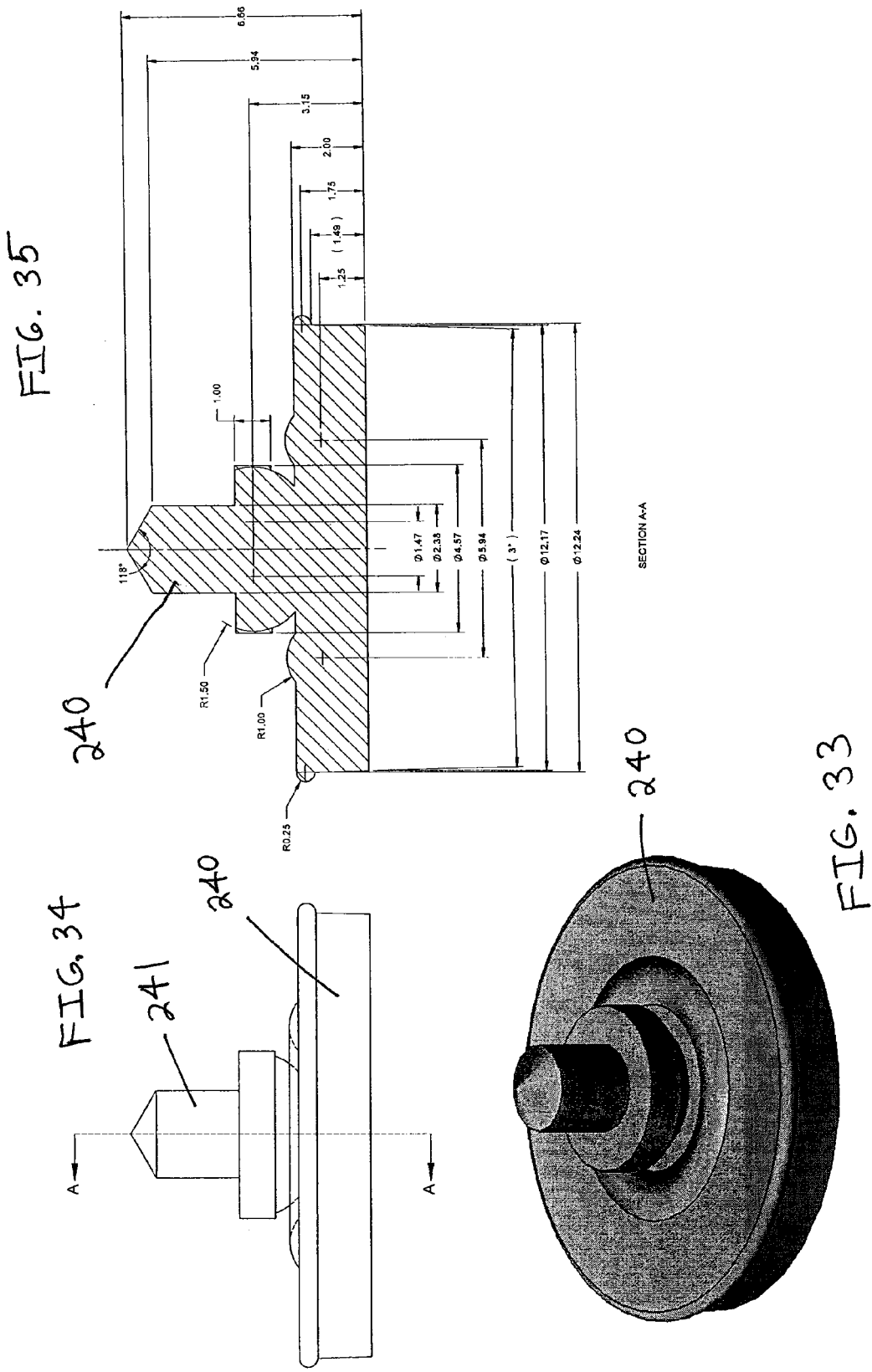

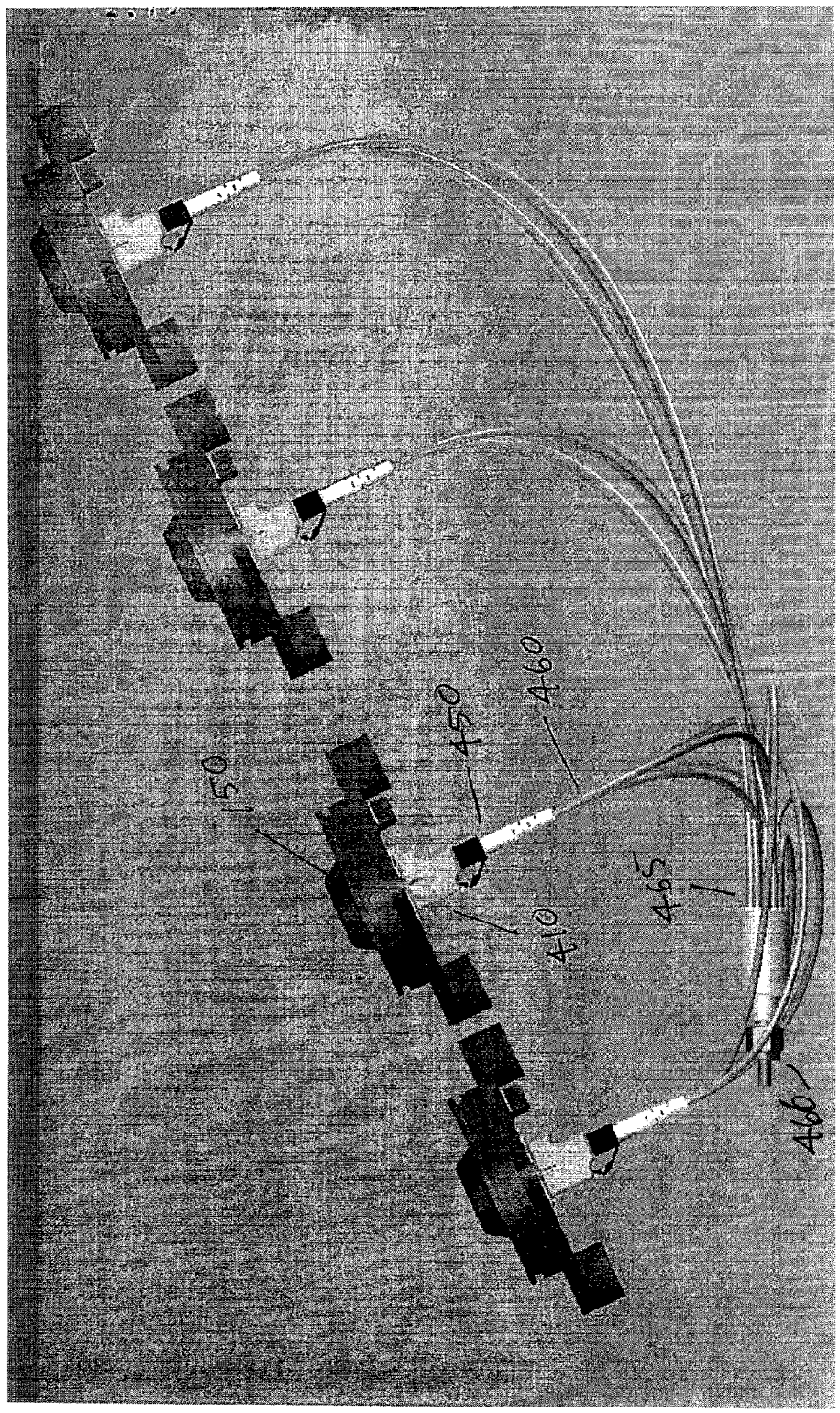

METHOD AND SYSTEM FOR DETECTING BIOLOGICAL MOLECULES IN SAMPLES

This application claims priority from U.S. Provisional Patent Application No. 61/356,384, filed Jun. 18, 2010, and incorporated herein by reference.

FIELD OF THE INVENTION

This invention relates to the field of detection methods and systems, and more specifically, to a method and system for detecting biological molecules in samples.

BACKGROUND

The ability to detect biological molecules associated with enzyme activity has application in fields such as testing for biological contamination of water and food products. Of particular interest is the ability to detect biological (e.g., bacterial) contamination of water. Several known methods for detection of bacteria such as *Escherichia coli* (*E. coli* or "EC") and total coliform ("TC") are based on detection of indicator enzyme activity in a broth designed to promote growth of the target organism. Accepted indicator enzymes are β-glucuronidase (β-glu) and β-galactosidase (β-gal) for EC and TC, respectively. Methods which use these enzymes rely on a reaction of the enzyme with a chromogenic or fluorogenic compound to measure the enzyme activity. In the case of β-glu or β-gal, usually a glucuronide or galactoside conjugate of a dye compound is added to the sample broth as a substrate, and if the target enzymes are present, the conjugate is converted to a free dye molecule. The enzyme-dependent conversion is detected by a change in colour or fluorescence of the free dye molecule compared to the conjugate. Some methods use soluble products detected in solution, with the coliform cells usually also suspended in solution. Others methods use coliform cells on the surface of a filter, membrane, or gel, usually with an insoluble dye product which adsorbs onto the support to form a coloured or fluorescent spot around colonies of target organisms. Some supported formats use multiple dye substrates which produce a variety of colours depending on which organisms are present.

However, the above methods are vulnerable to sources of error, such as suitability of broth and incubation conditions for all target coliform types, as well as presence of non-target organisms which may contribute to the indicator enzyme activity. Nonetheless, the reliability of established methods is high enough that there is broad regulatory acceptance of these methods for assessment of samples ranging from meat products to drinking water.

Further, in routine or commercial uses of such substrates, detection is usually done visually by human eye, which presents significant limitations in performance. A large number of coliform cells must be present before enough substrate will be converted for the product to be visible. This requires significant incubation and growth for detection of a small initial number of cells, and a standard 100 mL sample is incubated for 24 hours to provide a detection limit of one coliform cell in the initial sample. In some cases, more rapid detection is possible, but normally only with a higher detection limited accepted (e.g., 100 to 300 cells in a 100 mL sample). Also, visual detection is not quantitative, and these tests are normally used in a "presence/absence" mode where the actual number of coliform cells is not determined unless a more complex "most-probable number" method is used. Exceptions to the latter are some plating methods, where the number of colonies is counted and therefore the number of cells in the sample quantitatively determined. This, however, is a very labour-intensive, time-consuming process which also requires long incubation, and has limited dynamic range.

U.S. Pat. No. 7,402,426 to Brown, et al., which is incorporated herein by reference, provides a solution to several of the above shortcomings. In particular, Brown et al. provides a system for detecting presence of an organism having at least one enzyme in a sample, comprising: a vessel for incubating the sample and at least one substrate such that the at least one enzyme can react with the at least one substrate to produce a biological molecule; a solid partitioning element that allows partitioning of only one of said biological molecule and the at least one substrate thereinto, the partitioning element not including an indicator agent that interacts with the biological molecule or the at least one substrate; an excitation light source that irradiates the biological molecule or the at least one substrate partitioned into the partitioning element; a detector that detects fluorescence of the biological molecule or the at least one substrate partitioned into the partitioning element; and, a control unit; wherein the detected fluorescence is indicative of presence of the organism in the sample.

However, due to the demand for such testing, a need exists to improve the efficiency at which samples can be tested using systems such as Brown et al.

A need therefore exists for an improved method and system for detecting biological molecules in samples. Accordingly, a solution that addresses, at least in part, the above and other shortcomings is desired.

SUMMARY OF THE INVENTION

According to one aspect of the invention, there is provided a system for detecting presence of an organism having an enzyme in a sample, comprising: a cartridge for containing the sample and a substrate such that the enzyme can react with the substrate to produce a biological molecule; a partitioning element mounted in a recess in a base of the cartridge, the partitioning element allowing partitioning of the biological molecule thereinto; a light source for irradiating the biological molecule partitioned into the partitioning element; and, a detector for detecting fluorescence of the biological molecule partitioned into the partitioning element, the detected fluorescence being indicative of presence of the organism in the sample; wherein the light source is in a raised cartridge mount of the system that mates with the recess in the base of the cartridge.

In accordance with further aspects of the present invention there is provided a method, an apparatus such as a test system, a method for adapting this system, as well as articles of manufacture such as a computer readable medium (or product) having program instructions recorded thereon for practising the method of the invention.

BRIEF DESCRIPTION OF THE DRAWINGS

Features and advantages of the embodiments of the present invention will become apparent from the following detailed description, taken in combination with the appended drawings, in which:

FIG. 12 is a front perspective view illustrating a test cartridge with its lid in a held closed position in accordance with an embodiment of the invention;

FIG. 13 is a front perspective view illustrating the test cartridge of FIG. 12 with its lid in an opened position in accordance with an embodiment of the invention;

FIG. 14 is a front perspective view illustrating the test cartridge of FIG. 12 with its lid in a locked closed position in accordance with an embodiment of the invention;

FIGS. 25 and 26 are screen captures illustrating positive test result screens of a GUI of the test system in accordance with an embodiment of the invention;

FIGS. 27 and 28 are screen captures illustrating negative test result screens of a GUI of the test system in accordance with an embodiment of the invention;

FIGS. 33-35 are perspective, front, and cross sectional views, respectively, illustrating an alternate partitioning element in accordance with an embodiment of the invention; and, FIGS. 36-40 are perspective, bottom, front, rear, and side views, respectively, illustrating fiber optic bundling in accordance with an embodiment of the invention.

It will be noted that throughout the appended drawings, like features are identified by like reference numerals.

DETAILED DESCRIPTION OF THE EMBODIMENTS

In the following description, details are set forth to provide an understanding of the invention. In some instances, certain software, circuits, structures and methods have not been described or shown in detail in order not to obscure the invention. The term "biological molecule" is used herein to refer to any molecule which can function as a substrate of an enzymatic reaction, or any molecule that can be produced by an enzymatic reaction, regardless of whether the molecule is found in nature. The term "data processing system" is used herein to refer to any machine for processing data, including the computer systems and network arrangements described herein. Aspects of the present invention may be implemented in any computer programming language provided that the operating system of the data processing system provides the facilities that may support the requirements of the present invention. Any limitations presented would be a result of a particular type of operating system or computer programming language and would not be a limitation of the present invention. Aspects of the present invention may also be implemented in hardware or in a combination of hardware and software.

Figure 1:
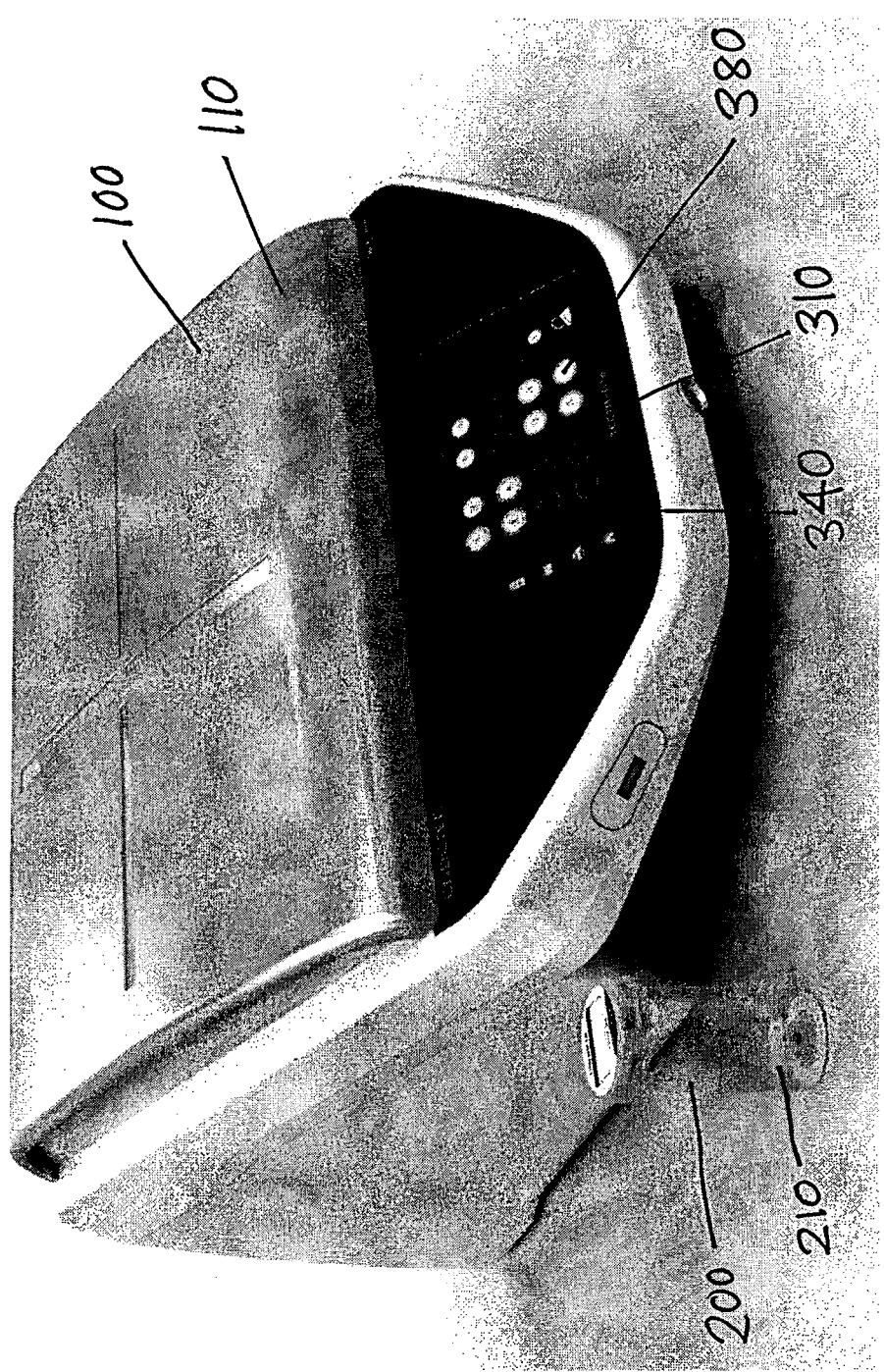
FIG. 1 is a front perspective view illustrating a test system with its lid in a closed position and a test cartridge in accordance with an embodiment of the invention.
Figure 2:
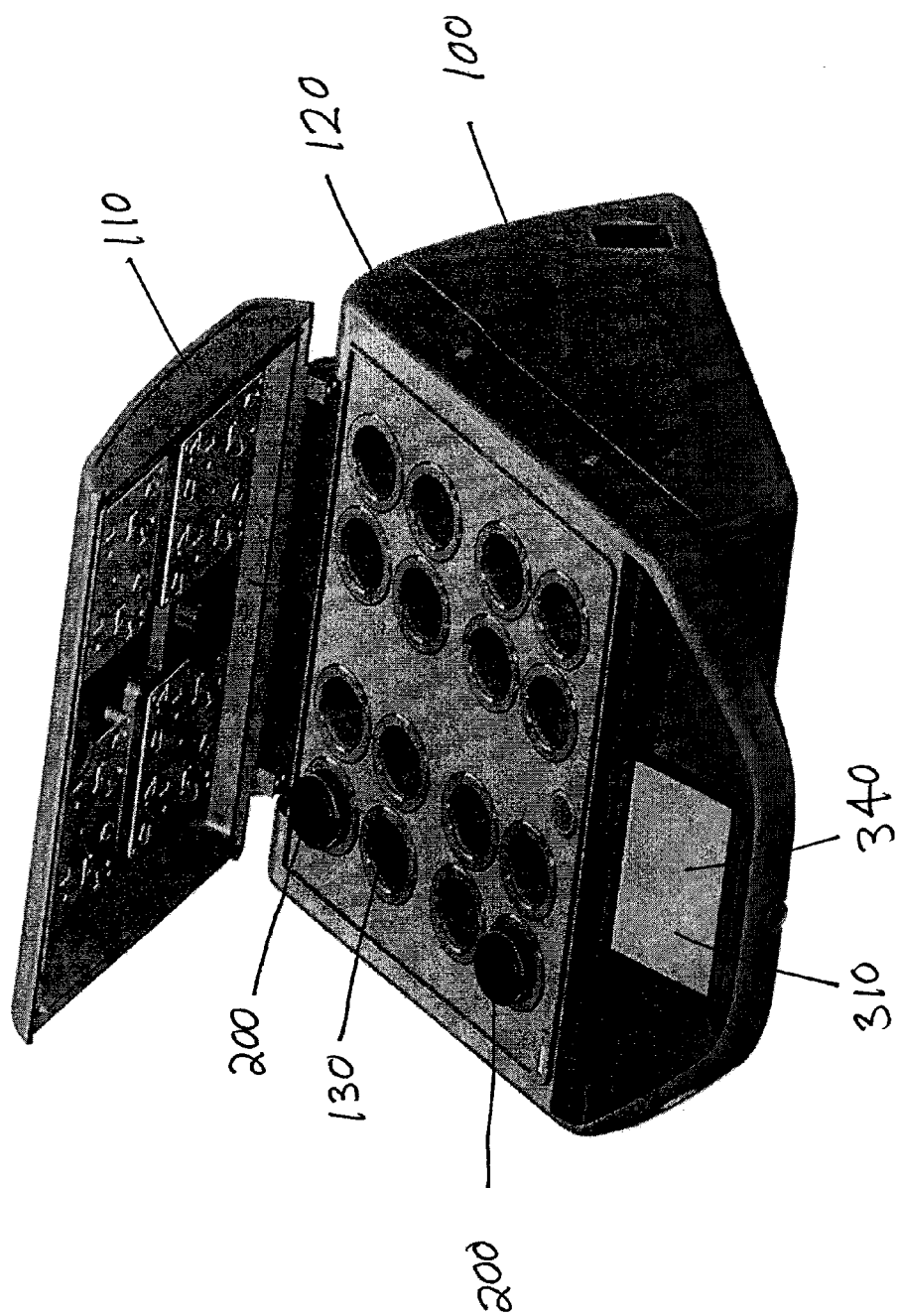
FIG. 2 is a front perspective view illustrating the test system of FIG. 1 with its lid in an opened position in accordance with an embodiment of the invention.
Figure 3:
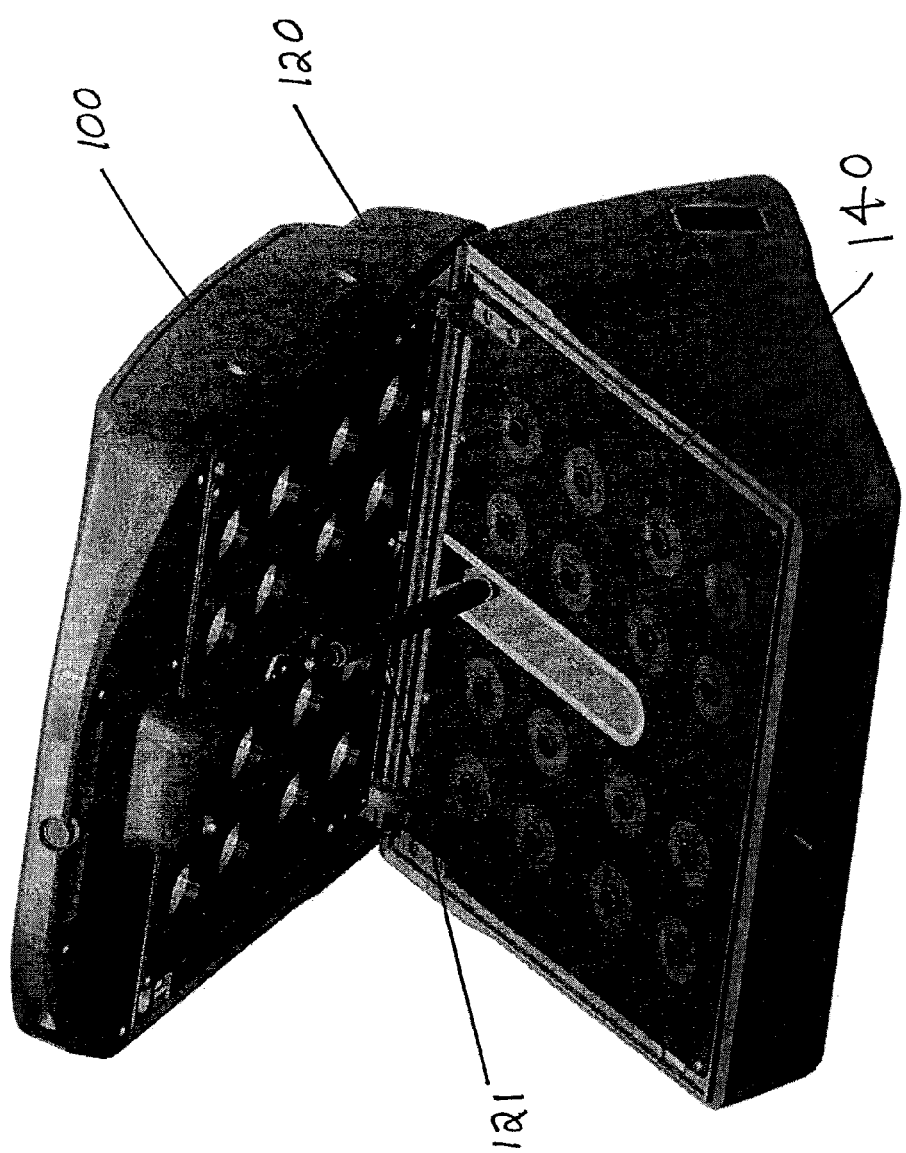
FIG. 3 is a front view illustrating the test system of FIG. 1 with its mantel in an opened position in accordance with an embodiment of the invention.
Figure 4:
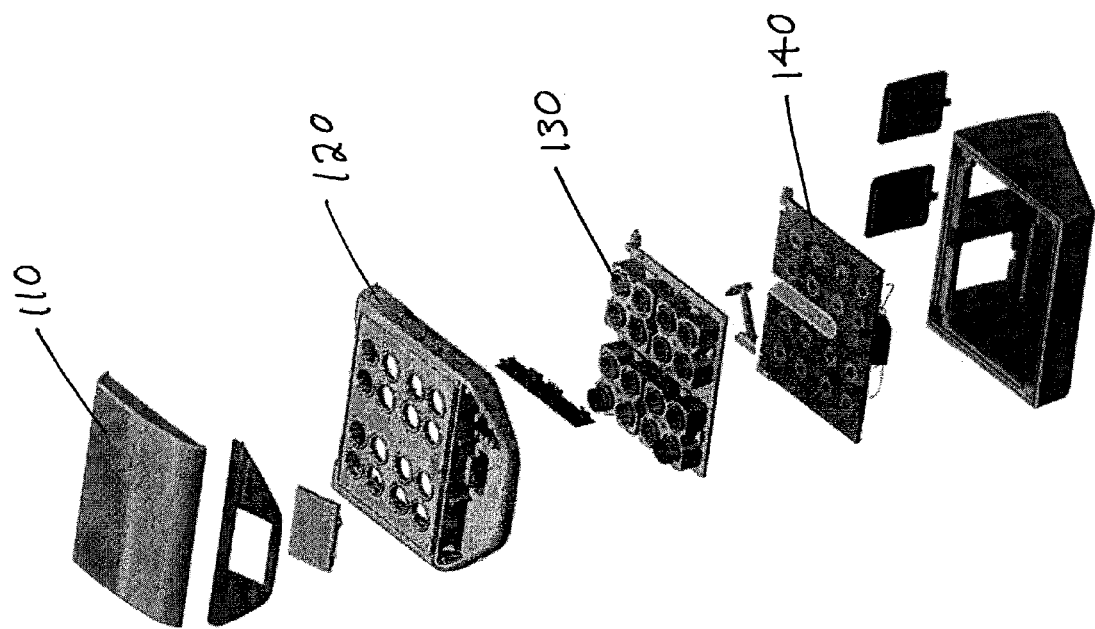
FIG. 4 is an expanded perspective view illustrating the test system of FIG. 1 in accordance with an embodiment of the invention.
Figure 5:
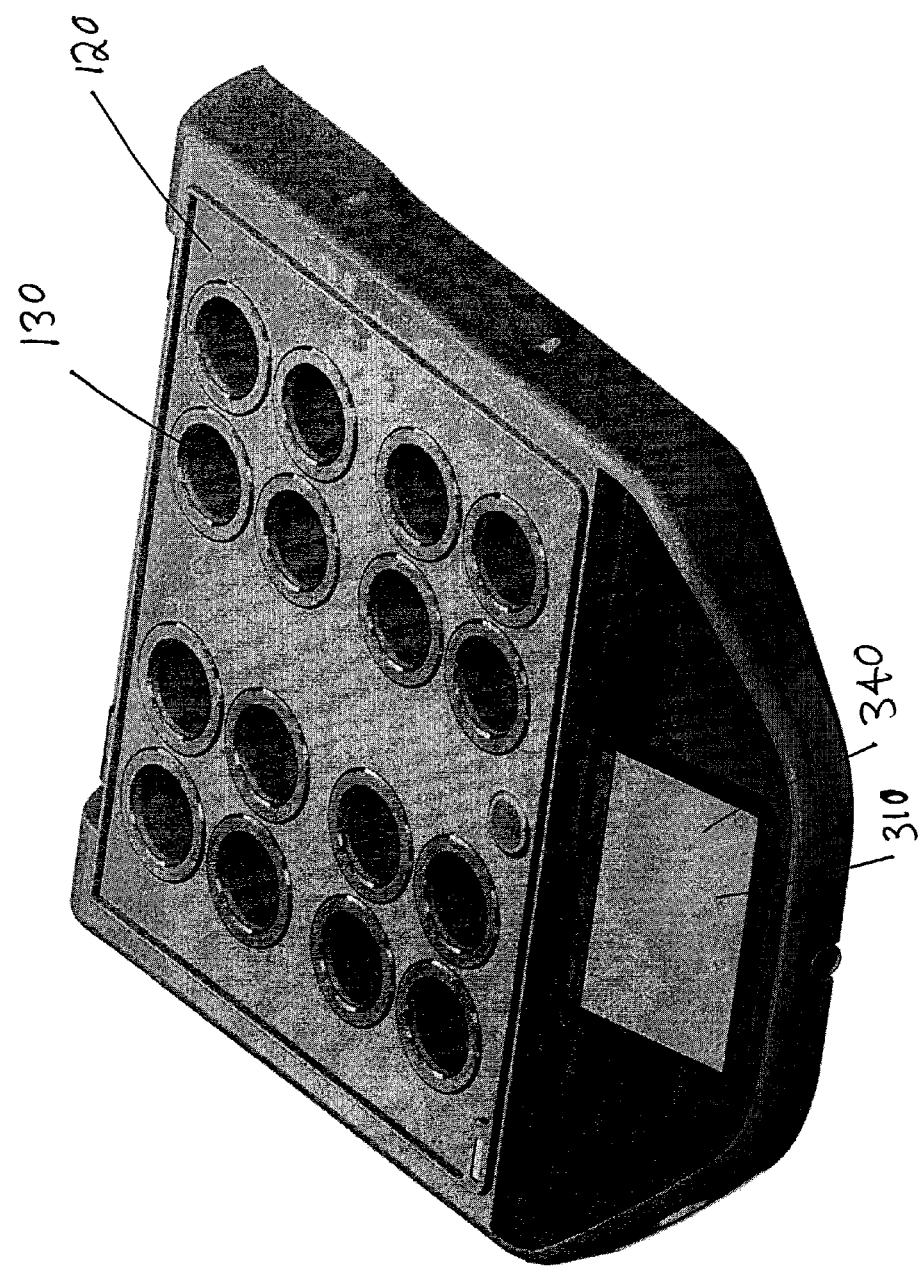
FIG. 5 is a front perspective view illustrating the mantel of the test system of FIG. 1 in accordance with an embodiment of the invention.
Figure 6:
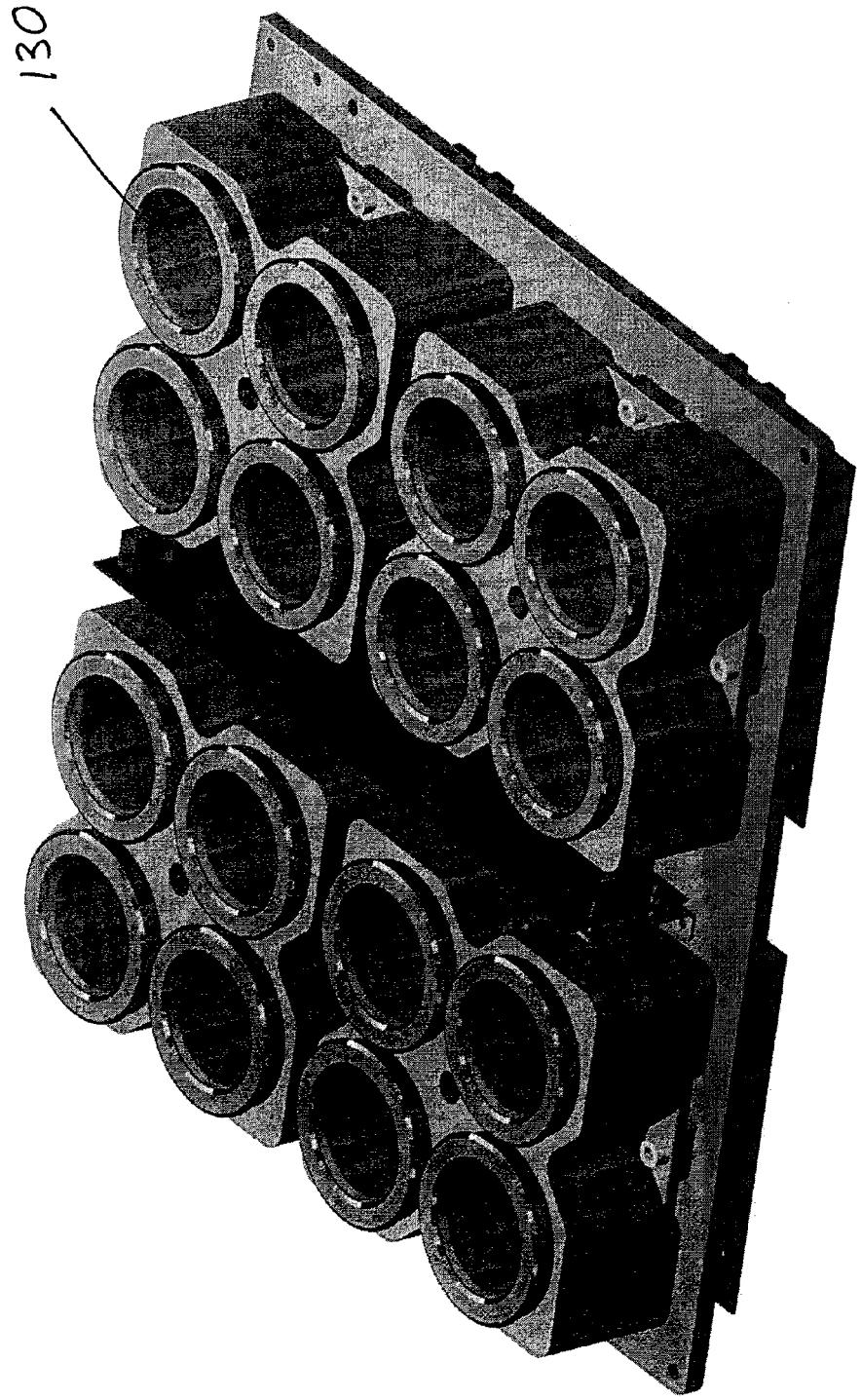
FIG. 6 is a front perspective view illustrating incubators within the mantel of FIG. 5 in accordance with an embodiment of the invention.

FIG. 1 is a front perspective view illustrating a test system 100 with its lid 110 in a closed position and a test cartridge 200 in accordance with an embodiment of the invention. FIG. 2 is a front perspective view illustrating the test system 100 of FIG. 1 with its lid 110 in an opened position in accordance with an embodiment of the invention. FIG. 3 is a front view illustrating the test system 100 of FIG. 1 with its mantel 120 in an opened position in accordance with an embodiment of the invention. FIG. 4 is an expanded perspective view illustrating the test system 100 of FIG. 1 in accordance with an embodiment of the invention. FIG. 5 is a front perspective view illustrating the mantel 120 of the test system 100 of FIG. 1 in accordance with an embodiment of the invention. And, FIG. 6 is a front perspective view illustrating incubators 130 within the mantel 120 of FIG. 5 in accordance with an embodiment of the invention.

According to one embodiment, a sample to be tested is placed in a test cartridge 200 which contains a substrate 210. The test cartridge 200 is then placed in an incubator or test chamber 130 in the mantel 120 of the test system 100. The lid 110 of the test system 100 may then be closed to begin a test for biological molecules associated with enzyme activity within the sample as will be described below. The incubator 130 may have a heating system associated therewith for heating the sample in the test cartridge 200. The mantel 120 may be hinge mounted within the test system 100 and may be opened to access an optical board 140 for cleaning and maintenance. A piston 121 may be used to keep the mantel 120 in an opened position. The test system 100 may be modular in design, as shown in FIG. 4, to facilitate cleaning, replacement, and maintenance of various modules or components (e.g., 120, 130, 140) of the test system 100.

According to one embodiment, cartridges 200 are held at an angle (e.g., 25 degrees) in the incubators 130 to minimize residue build-up on the optical elements and board 140 while avoiding contact of sample liquid with the lids of the cartridges 200. This may be accomplished by mounting the mantel 120 and optical board 140 at an angle within the test system 100.

Figure 7:
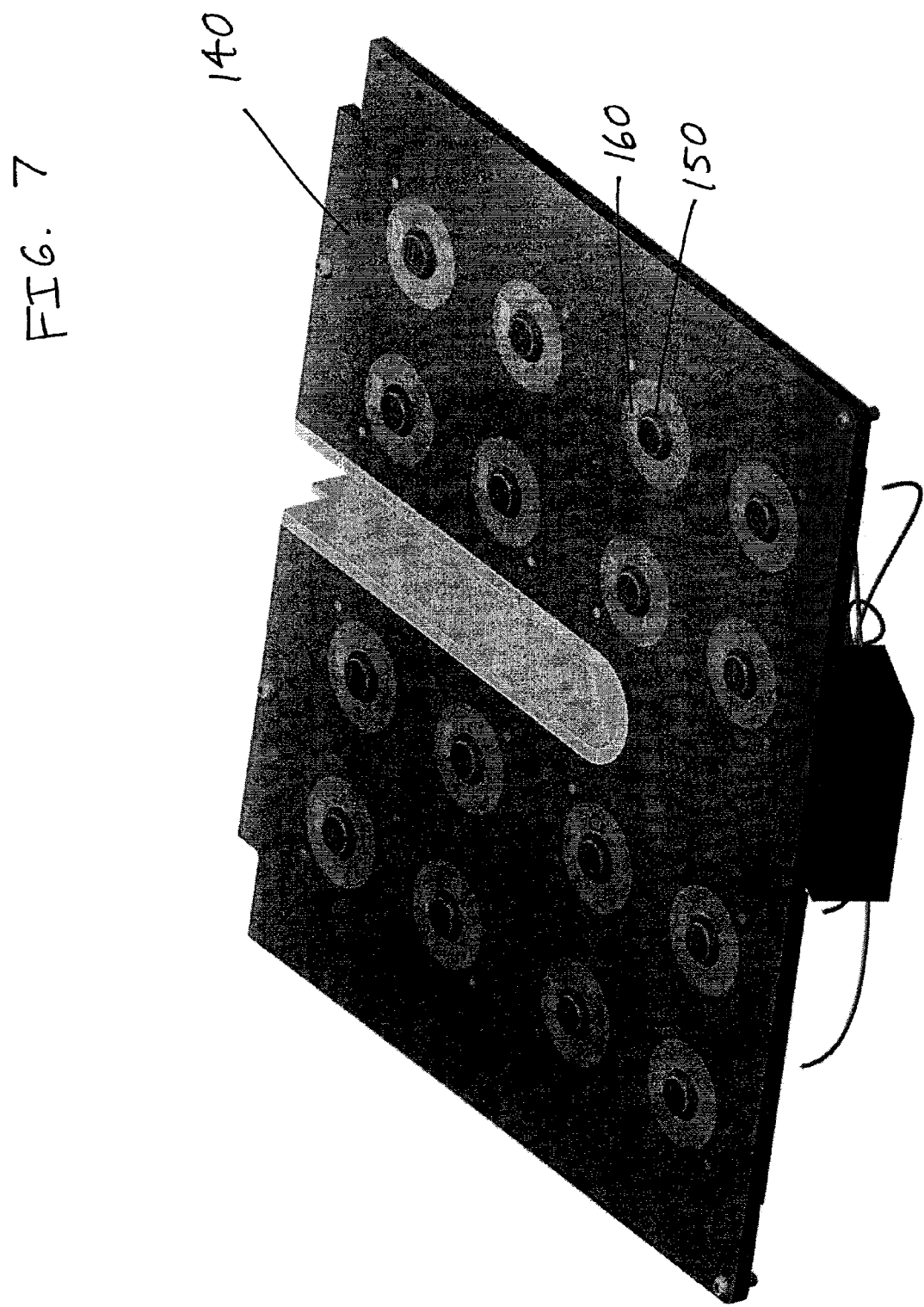
FIG. 7 is a front perspective view illustrating the upper surface of an optical board of the test system of FIG. 1 in accordance with an embodiment of the invention.
Figure 8:
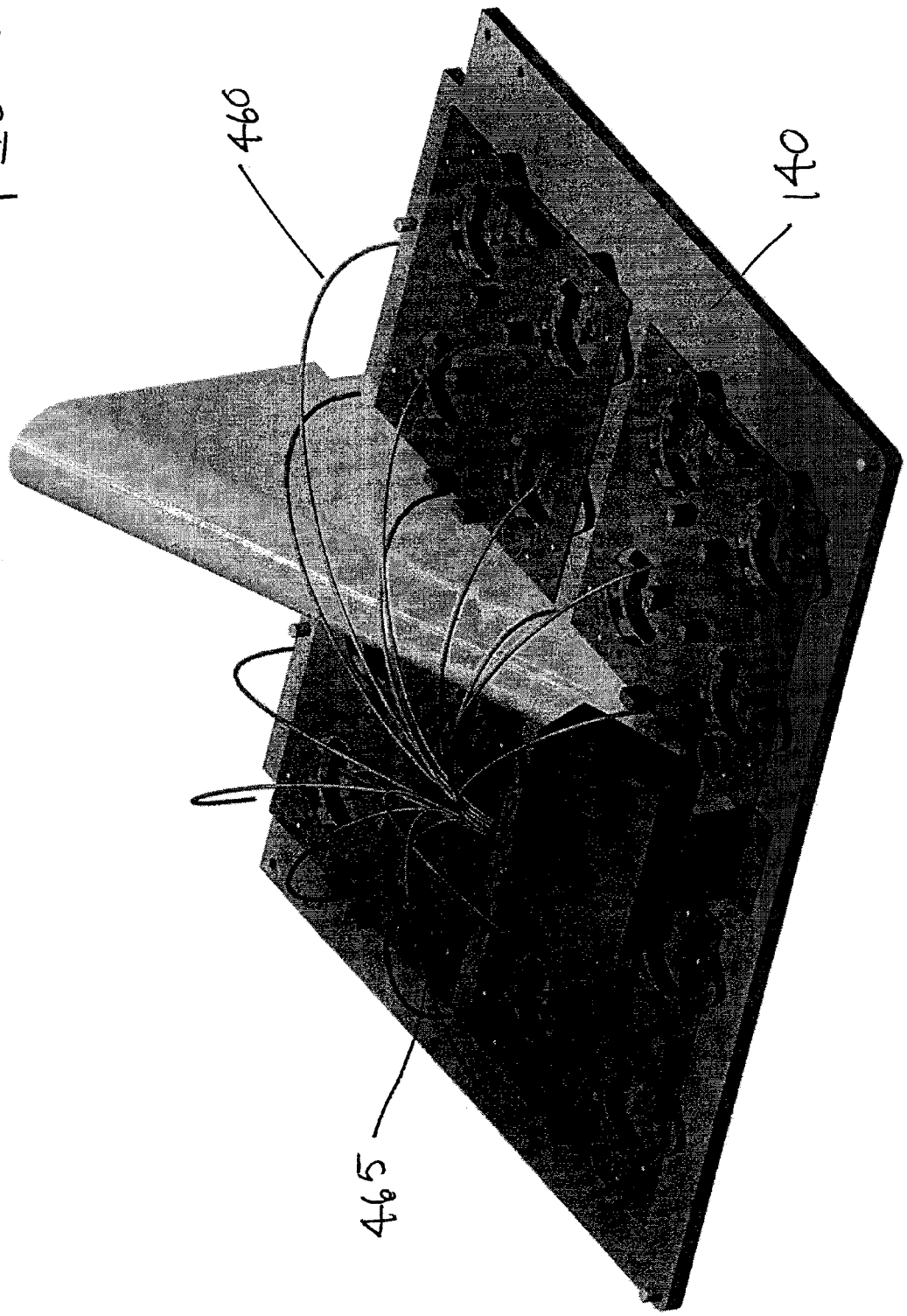
FIG. 8 is a front perspective view illustrating the lower surface of the optical board of FIG. 7 in accordance with an embodiment of the invention.
Figure 9:
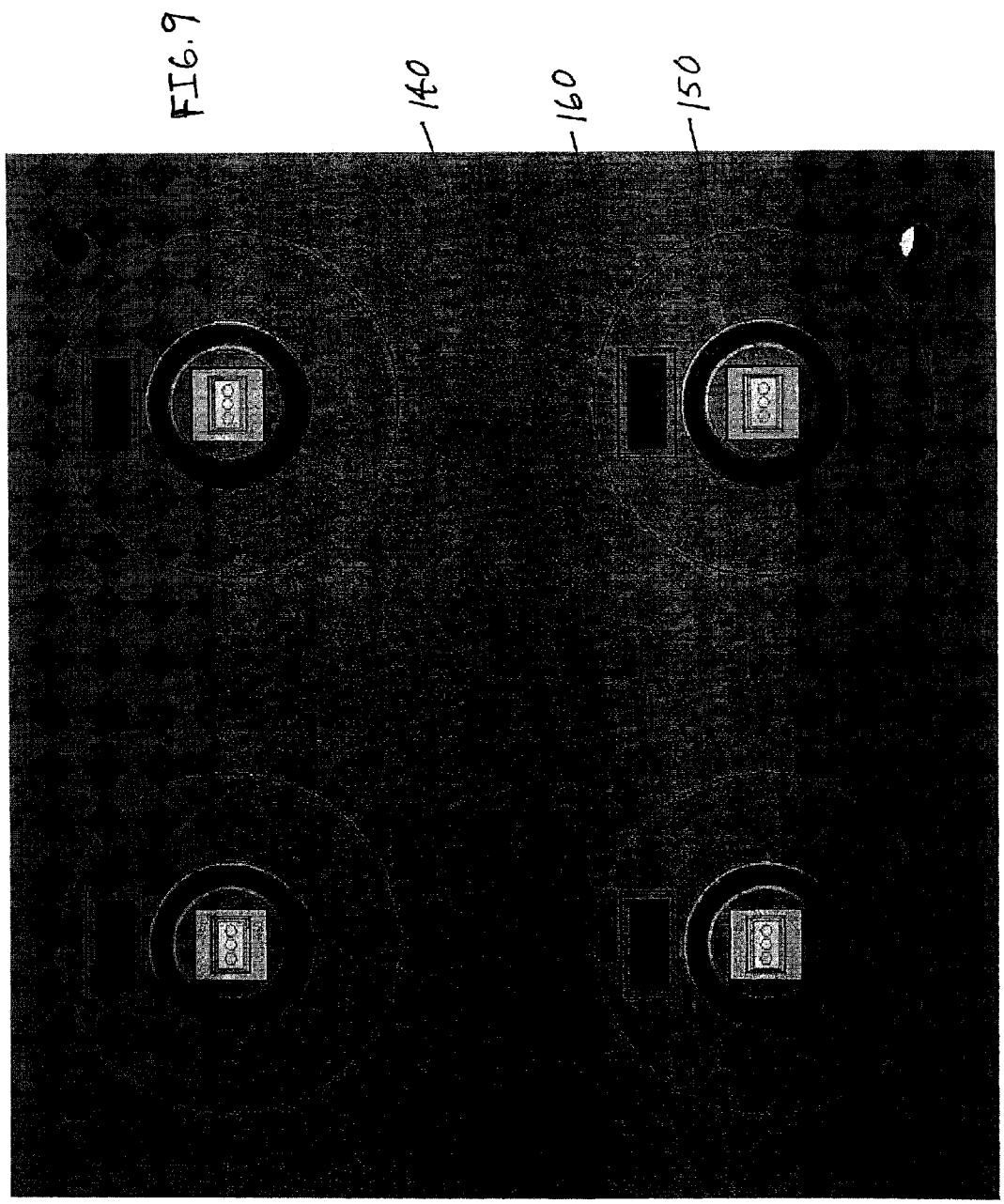
FIG. 9 is a top view illustrating a portion of the upper surface of the optical board of FIG. 7 in accordance with an embodiment of the invention.
Figure 10:
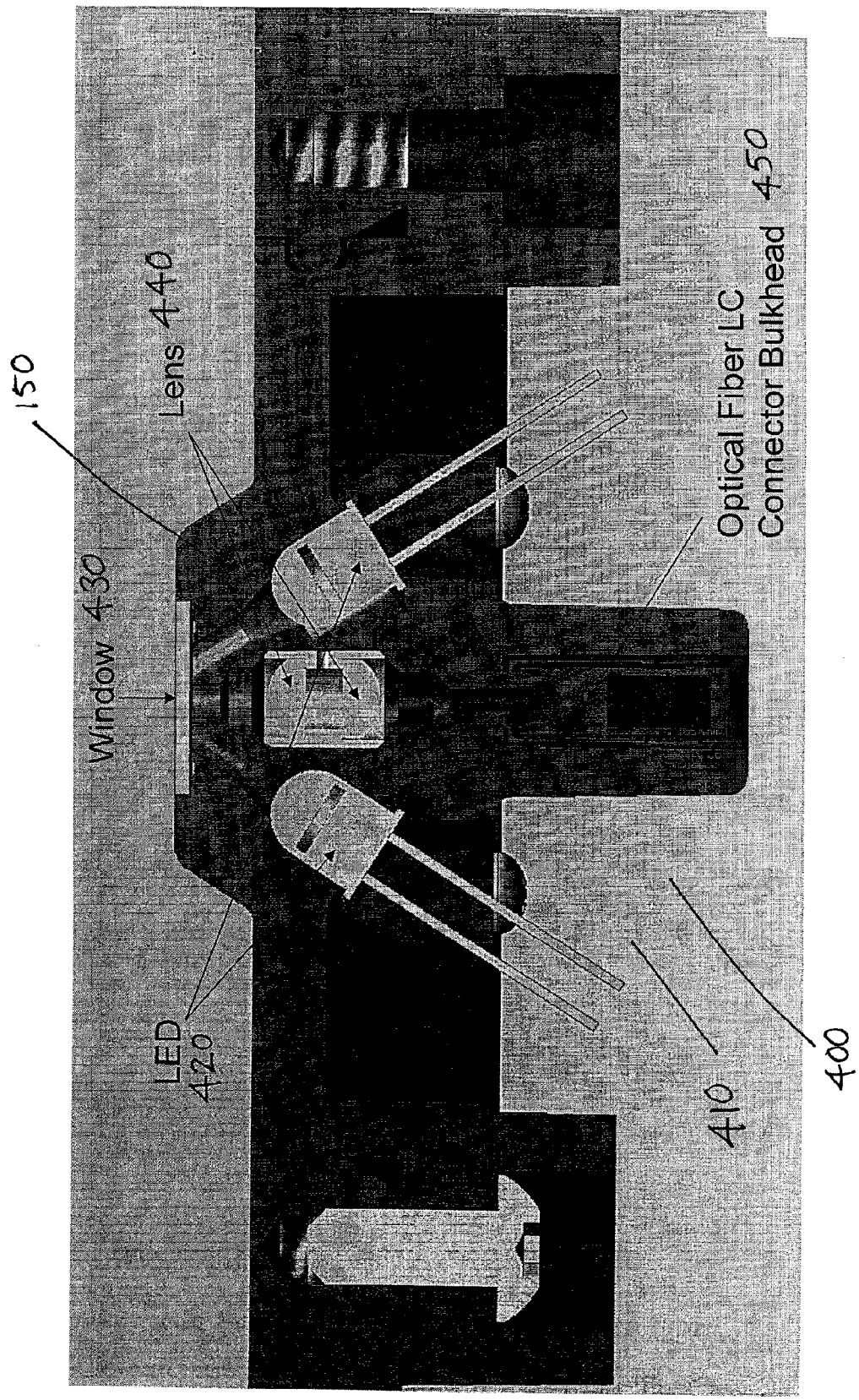
FIG. 10 is a cross sectional view illustrating a raised cartridge mount of the optical board of FIG. 7 in accordance with an embodiment of the invention.
Figure 11:
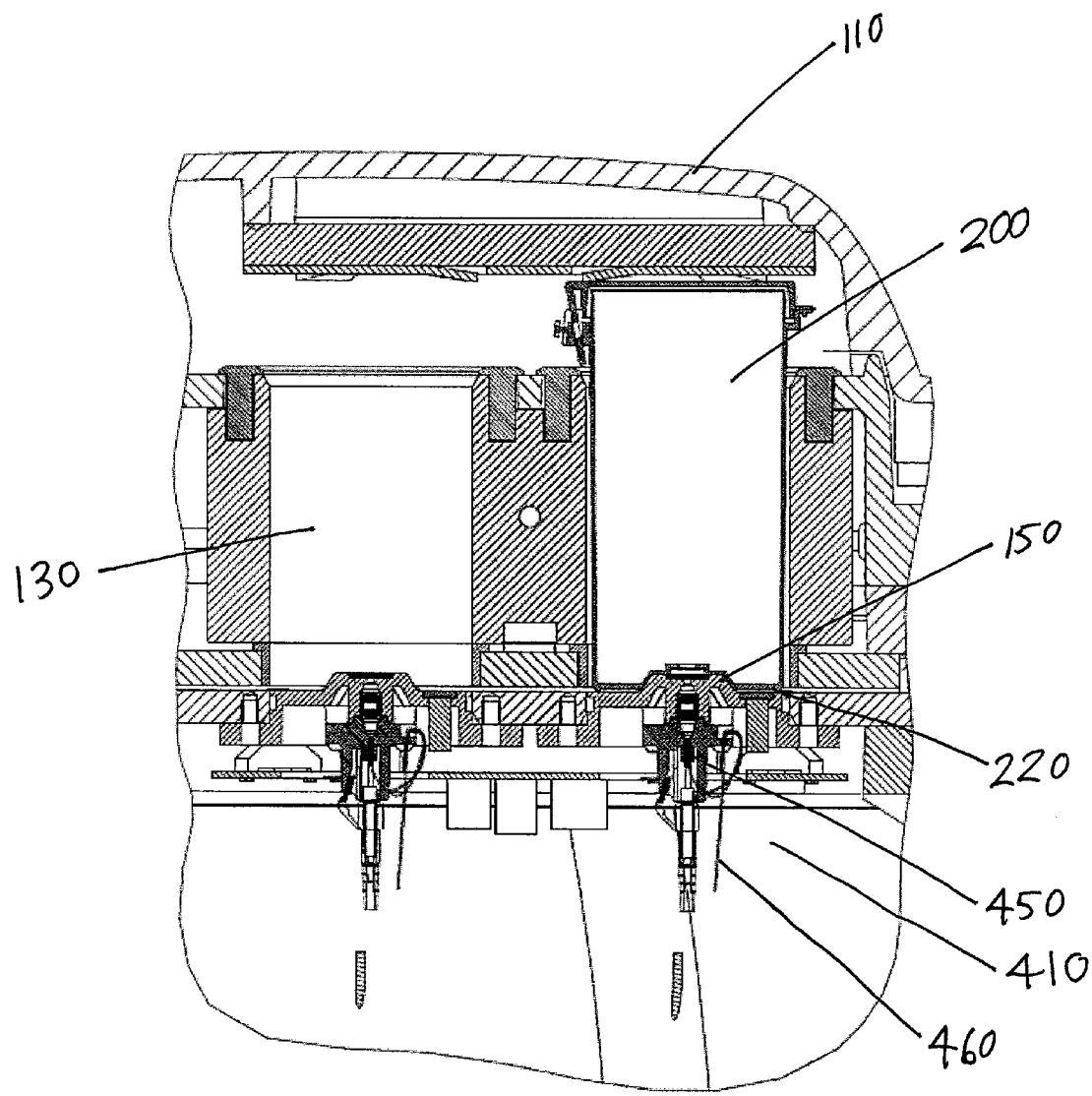
FIG. 11 is a partial cross sectional view illustrating a test cartridge installed on a raised cartridge mount in the test system of FIG. 1 in accordance with an embodiment of the invention.

FIG. 7 is a front perspective view illustrating the upper surface of an optical board 140 of the test system 100 of FIG. 1 in accordance with an embodiment of the invention. FIG. 8 is a front perspective view illustrating the lower surface of the optical board 140 of FIG. 7 in accordance with an embodiment of the invention. FIG. 9 is a top view illustrating a portion of the upper surface of the optical board 140 of FIG. 7 in accordance with an embodiment of the invention. FIG. 10 is a cross sectional view illustrating a raised cartridge mount 150 of the optical board 140 of FIG. 7 in accordance with an embodiment of the invention. And, FIG. 11 is a partial cross sectional view illustrating a test cartridge 200 installed on a raised cartridge mount 150 in the test system 100 of FIG. 1 in accordance with an embodiment of the invention.

Below the mantel 120 is an optical board 140 which has a raised cartridge mount 150 for each incubator 130. The raised cartridge mount 150 mates with the base 220 of a test cartridge 200 as will be described below. Each raised cartridge mount 150 may have an infra-red sensor 160 to detect whether a test cartridge 200 is present.

Figure 15:
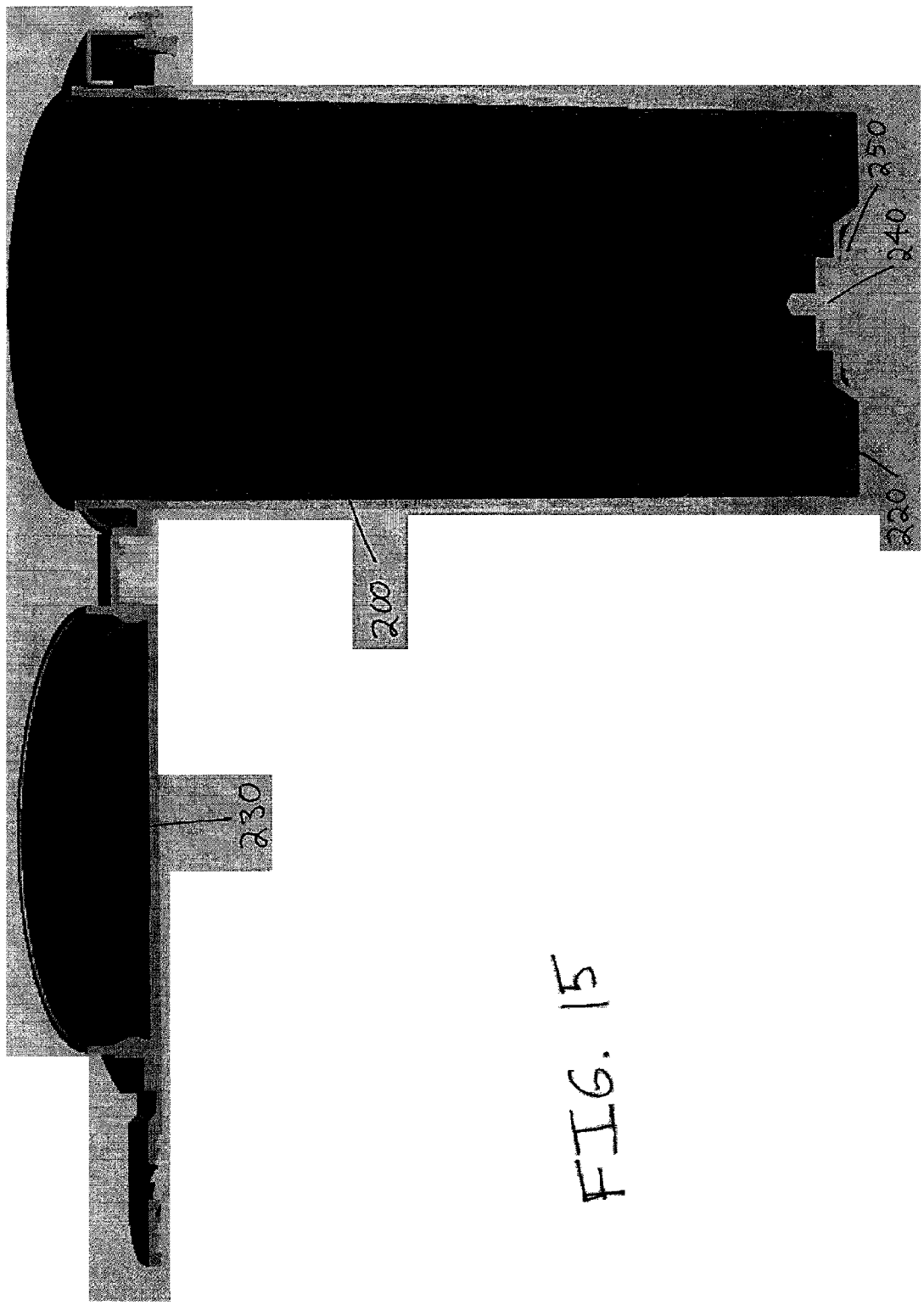
FIG. 15 is a cross sectional view illustrating the test cartridge of FIG. 12 with a partitioning element installed in accordance with an embodiment of the invention.
Figure 16:
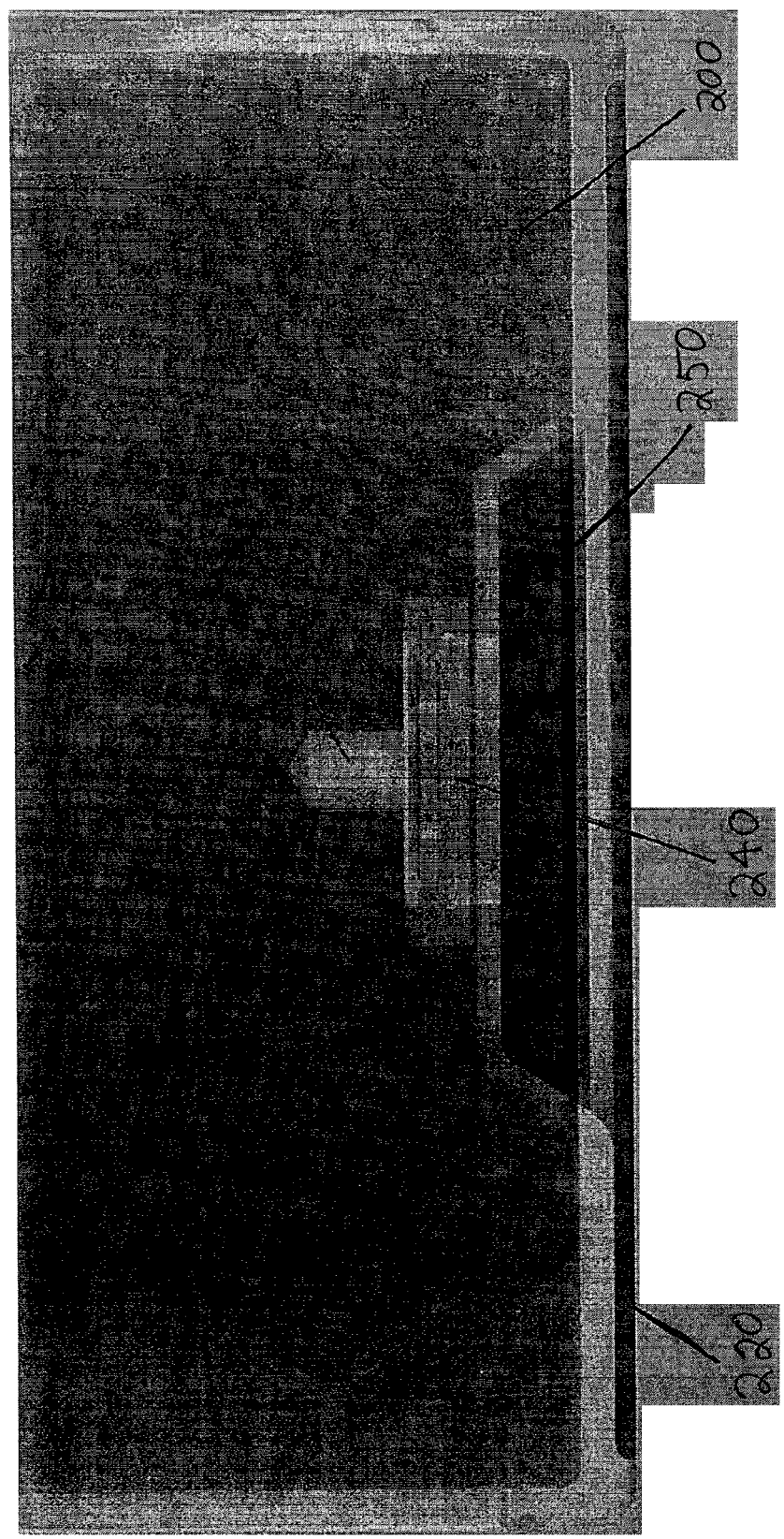
FIG. 16 is a cross sectional detail view illustrating the test cartridge of FIG. 12 with a partitioning element installed in accordance with an embodiment of the invention.
Figure 17:
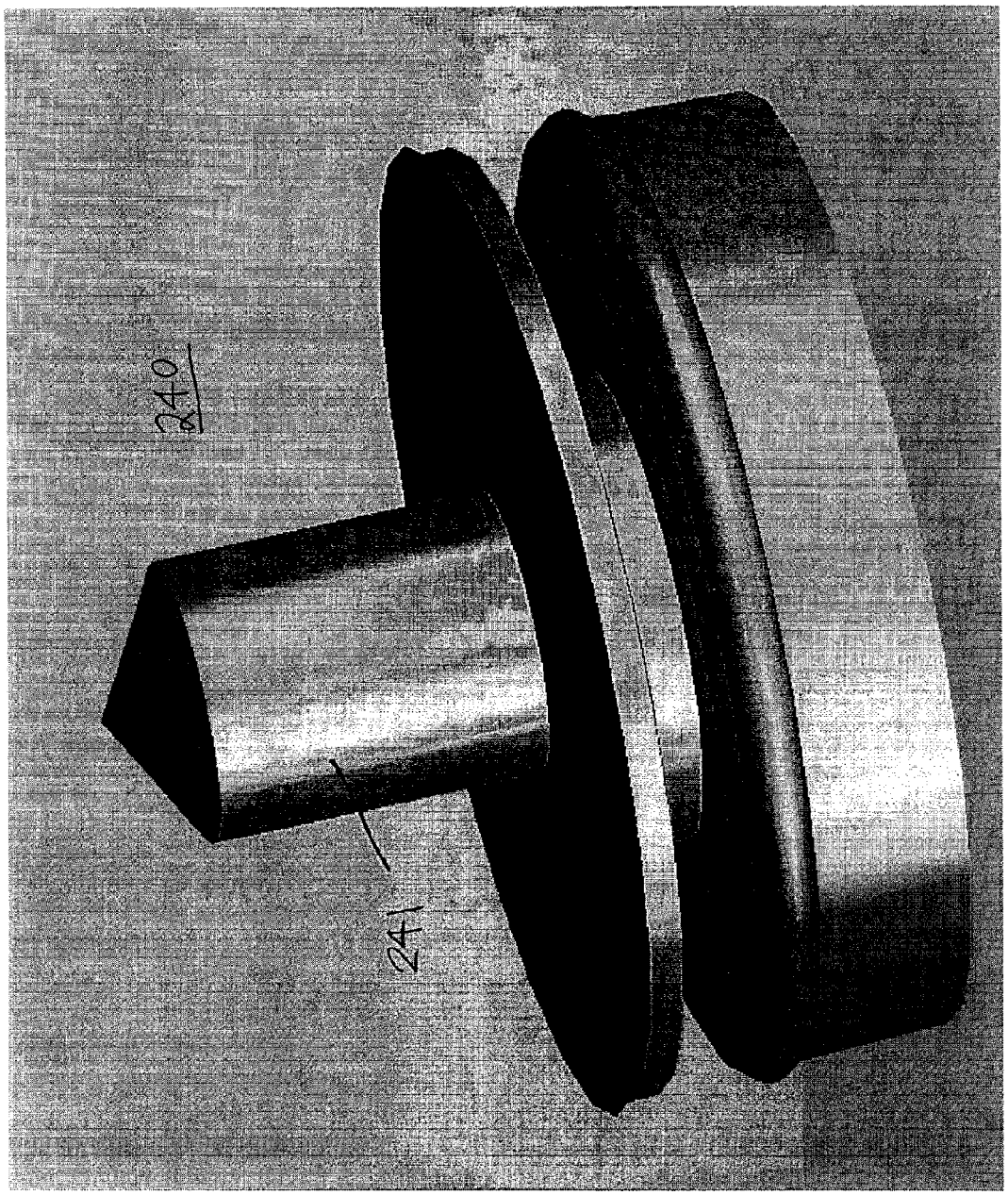
FIG. 17 is a front perspective view of a partitioning element in accordance with an embodiment of the invention.
Figure 18:
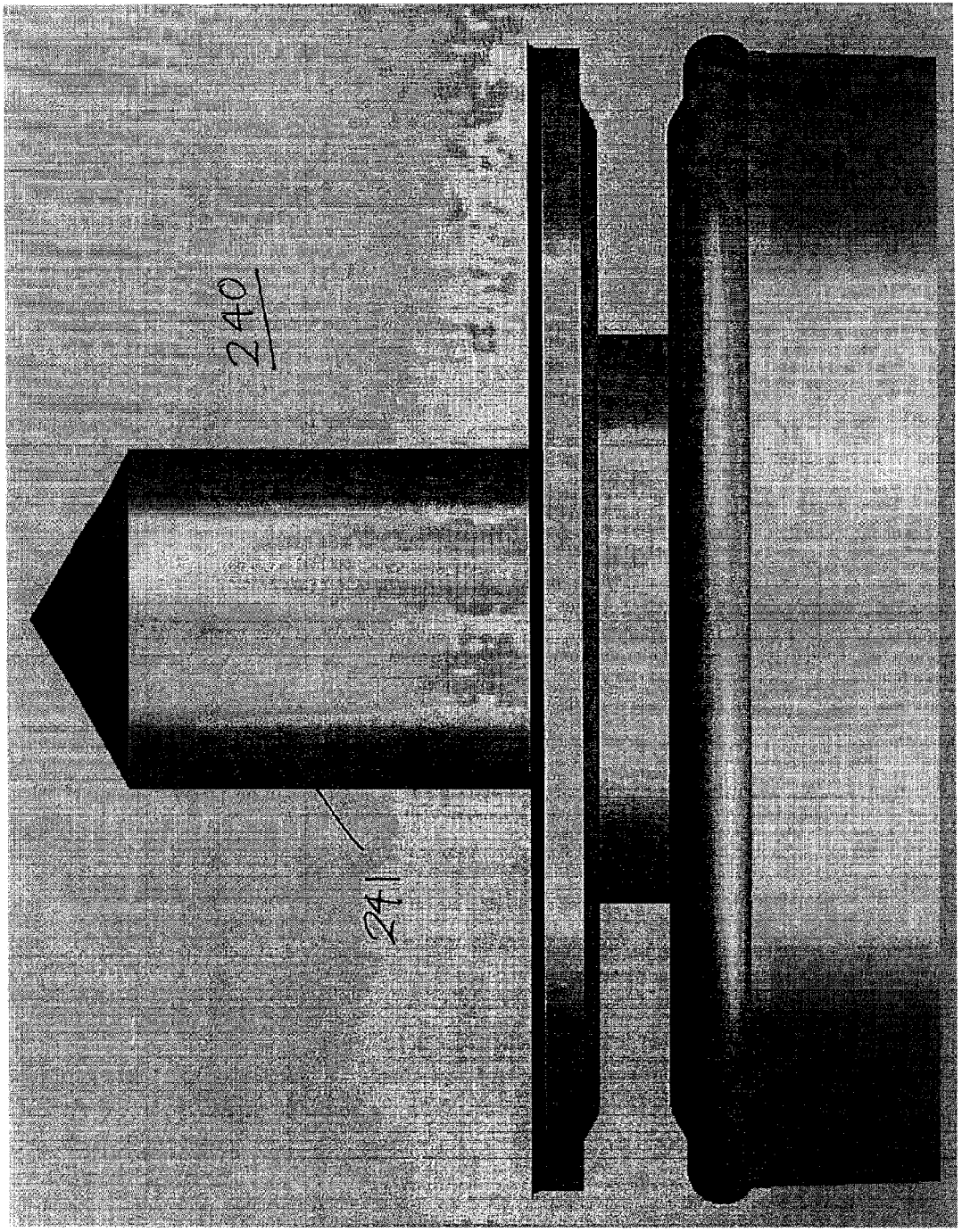
FIG. 18 is a front view of the partitioning element of FIG. 17 in accordance with an embodiment of the invention.
Figure 32:
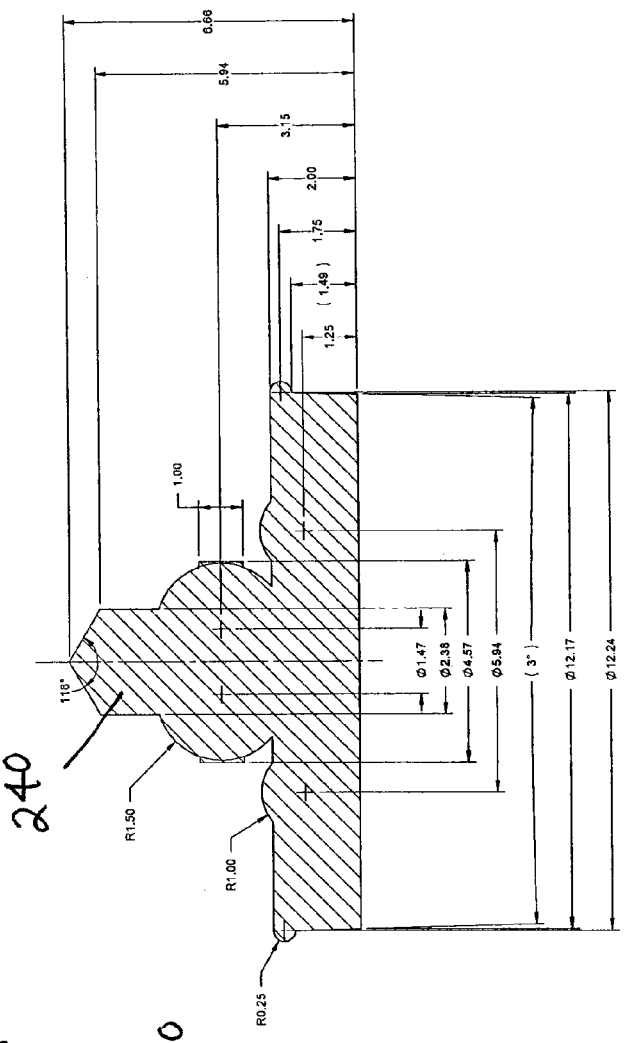
FIGS. 30-32 are perspective, front, and cross sectional views, respectively, illustrating an alternate partitioning element in accordance with an embodiment of the invention.
Figure 31:
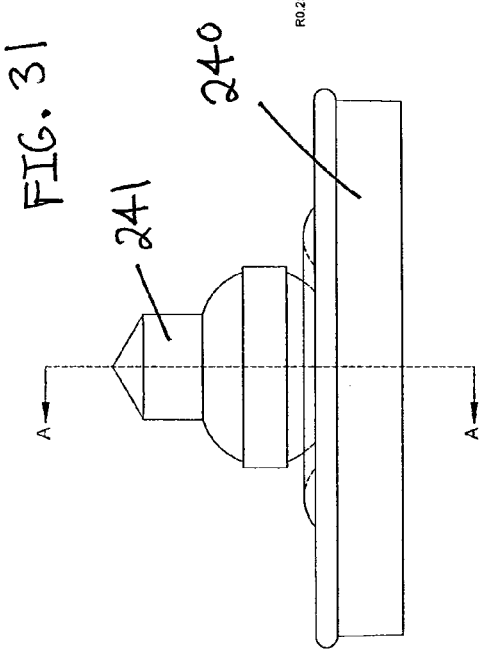
Figure 30:
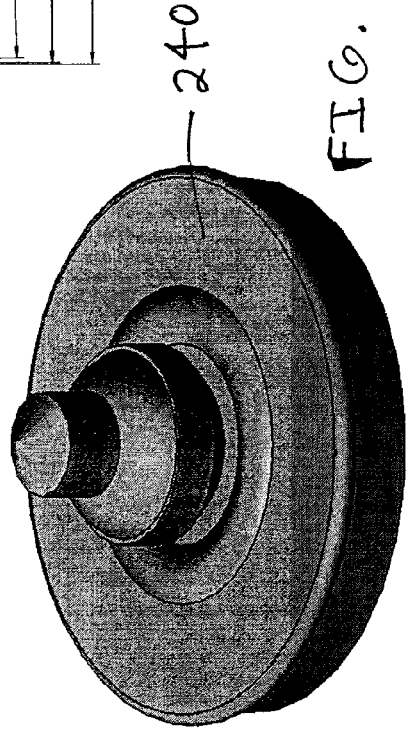
Figure 36:
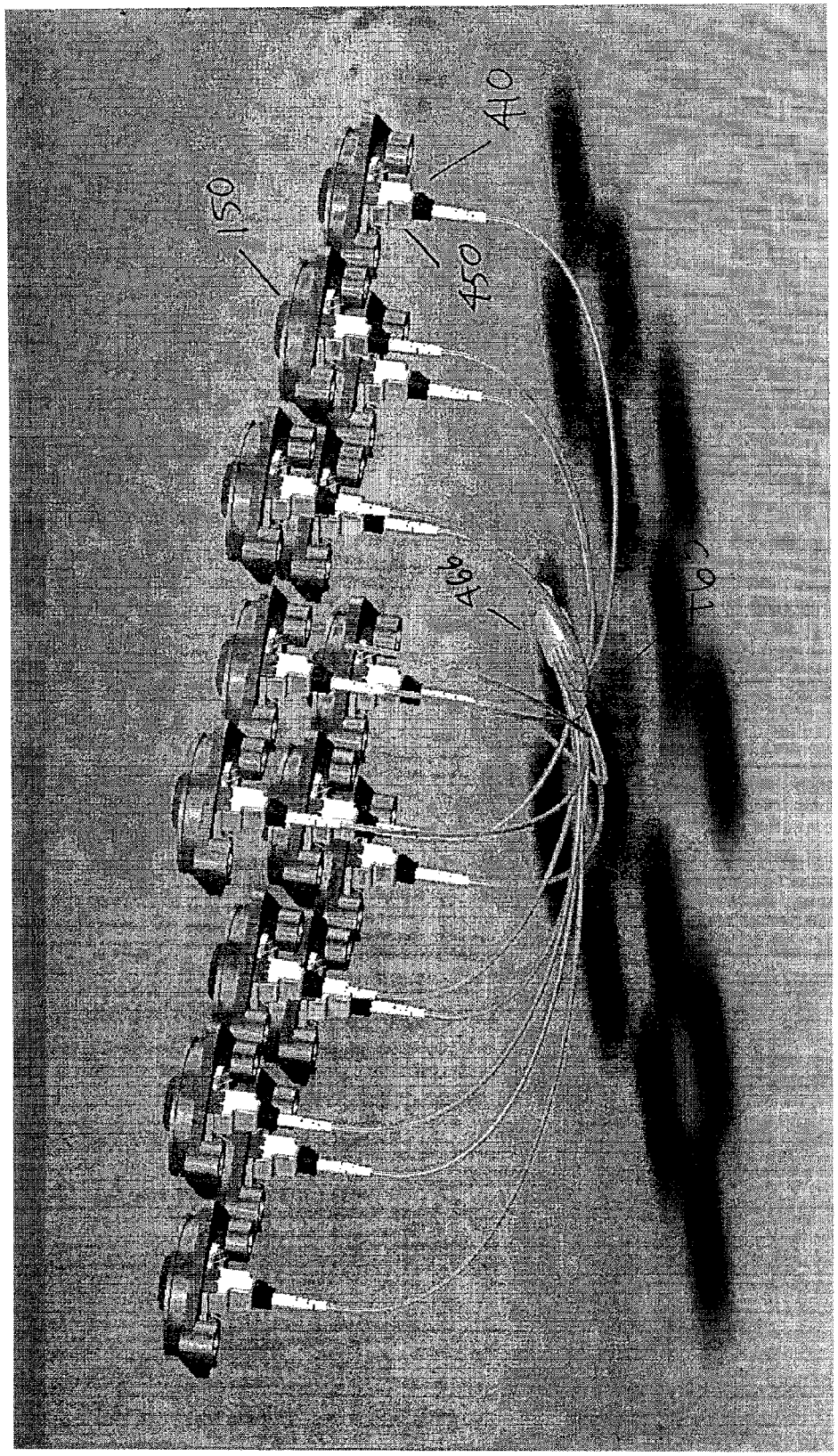
Figure 37:
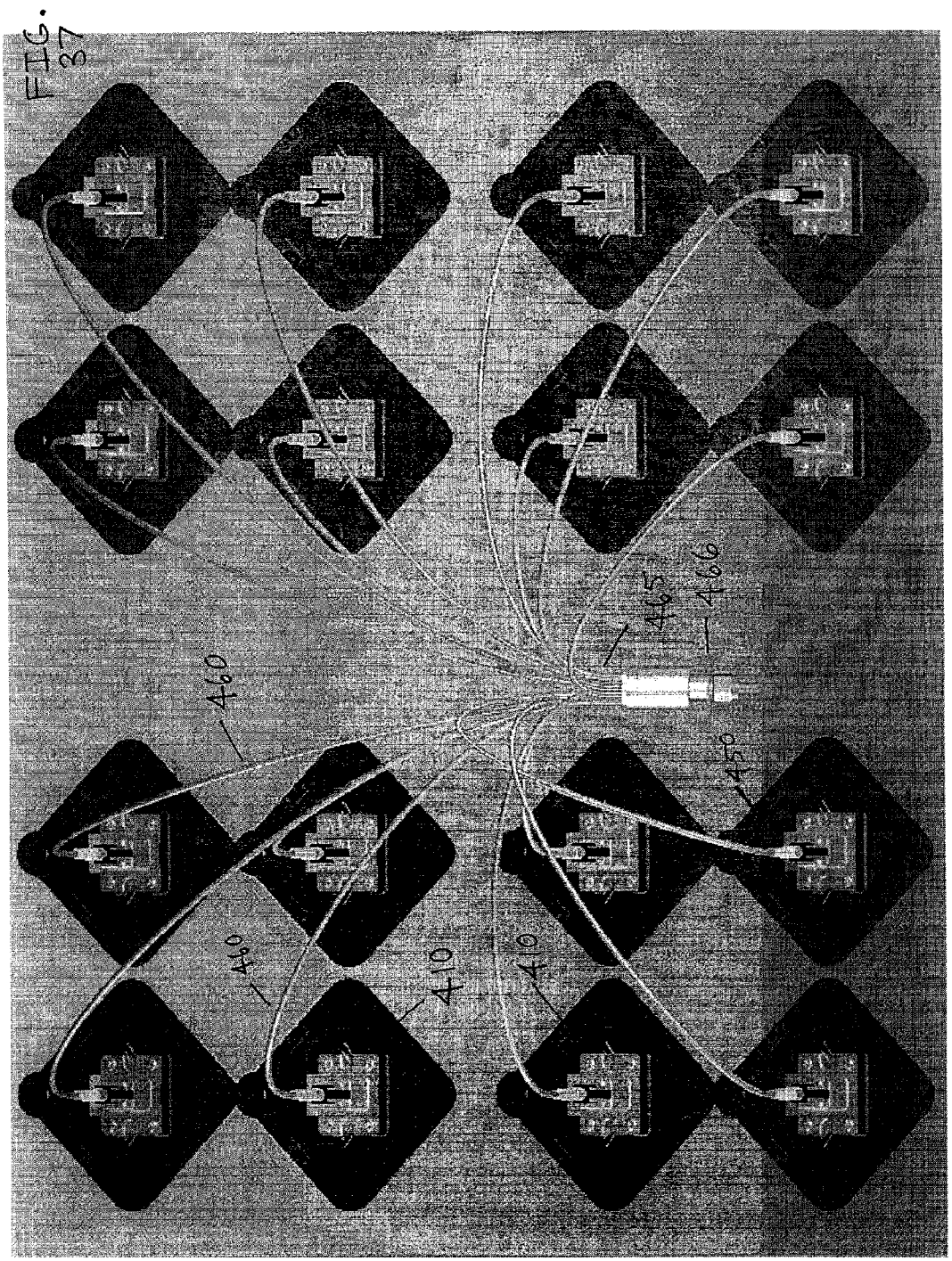
Figure 38:
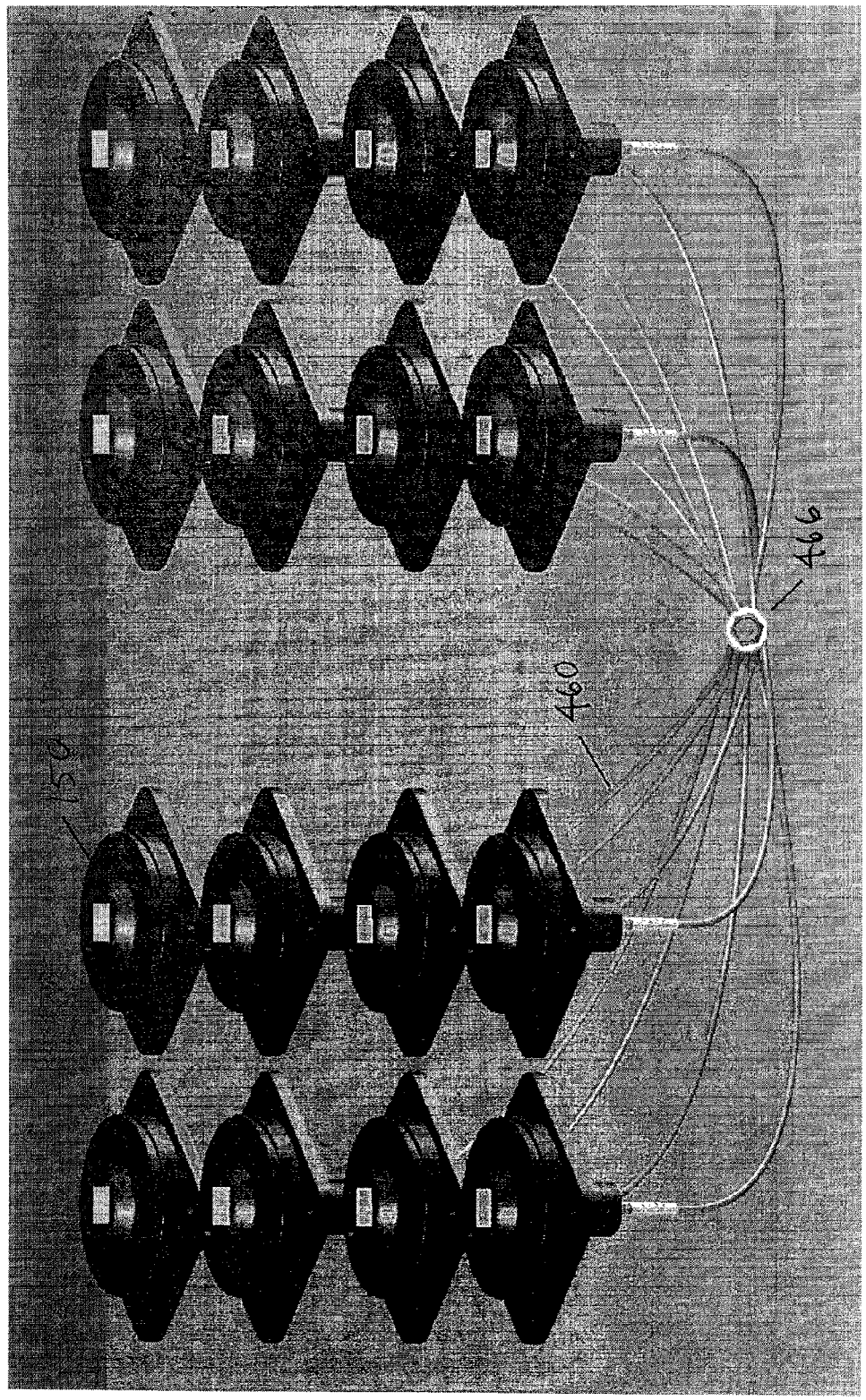
Figure 39:
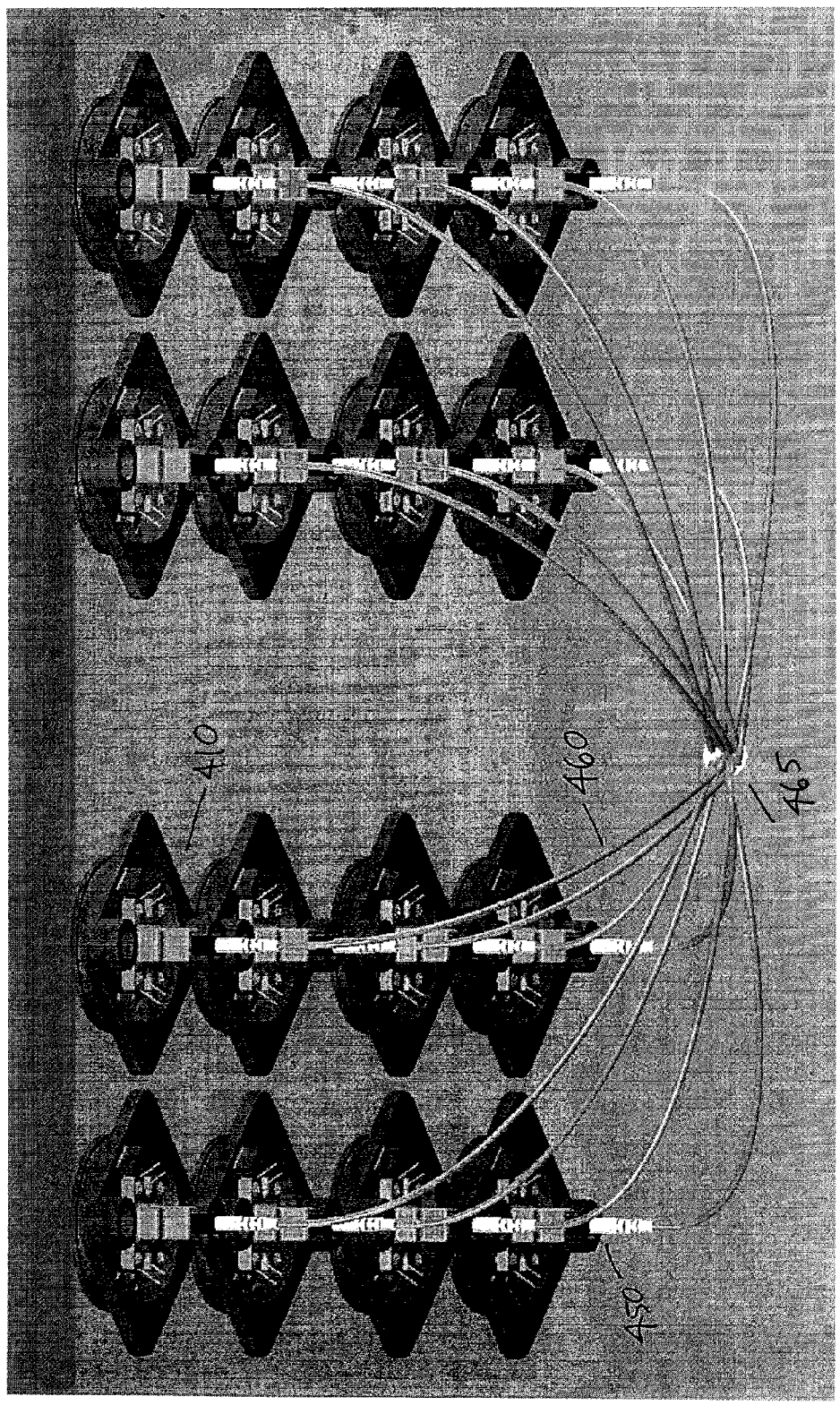

FIG. 12 is a front perspective view illustrating a test cartridge 200 with its lid 230 in a held closed position in accordance with an embodiment of the invention. FIG. 13 is a front perspective view illustrating the test cartridge 200 of FIG. 12 with its lid 230 in an opened position in accordance with an embodiment of the invention. FIG. 14 is a front perspective view illustrating the test cartridge 200 of FIG. 12 with its lid 230 in a locked closed position in accordance with an embodiment of the invention. FIG. 15 is a cross sectional view illustrating the test cartridge 200 of FIG. 12 with a partitioning element 240 installed in accordance with an embodiment of the invention. FIG. 16 is a cross sectional detail view illustrating the test cartridge 200 of FIG. 12 with a partitioning element 240 installed in accordance with an embodiment of the invention. FIG. 17 is a front perspective view of a partitioning element 240 in accordance with an embodiment of the invention. FIG. 18 is a front view of the partitioning element 240 of FIG. 17 in accordance with an embodiment of the invention. FIGS. 30-32 are perspective, front, and cross sectional views, respectively, illustrating an alternate partitioning element 240 in accordance with an embodiment of the invention. And, FIGS. 33-35 are perspective, front, and cross sectional views, respectively, illustrating an alternate partitioning element 240 in accordance with an embodiment of the invention.

Installed in the test cartridge 200 over a recess 250, mounted in the recess 250, molded into the recess 250, or snap fit into the recess 250 in the base 220 of the test cartridge 200 is a partitioning element 240. The partitioning element 240 may be a polymer partitioning element 240. The partitioning element 240 is in contact with the sample in the test cartridge 200 and is optically coupled to the optical system 400 described below.

Figure 19:
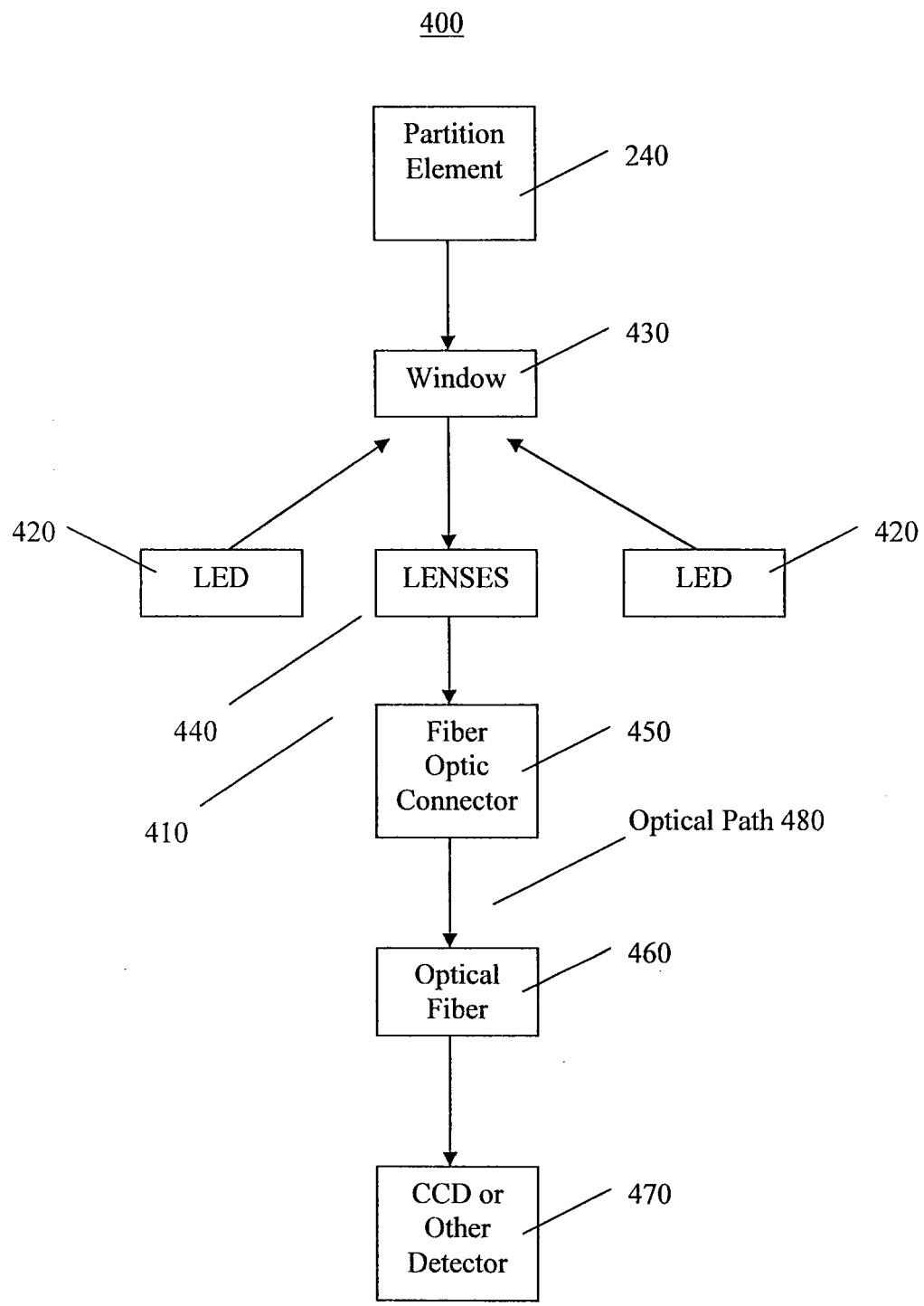
FIG. 19 is a block diagram illustrating an optical system of the test system in accordance with an embodiment of the invention.

FIG. 19 is a block diagram illustrating an optical system 400 of the test system 100 in accordance with an embodiment of the invention. FIGS. 36-40 are perspective, bottom, front, rear, and side views, respectively, illustrating fiber optic bundling 465 in accordance with an embodiment of the invention.

The test system 100 includes an optical system 400 which may include the optical board 140. The optical system 400 is used to detect fluorescence in the partitioning element 240. The optical system 400 in combination with the raised cartridge mount 150 is designed to receive and/or optimize the fluorescence signal derived from the polymer partitioning element 240 in the test cartridge 200.

In particular, the raised cartridge mount 150 is designed to fit into a matched recess 250 formed in the base 220 of the test cartridge 200 to centre the polymer partitioning element 240 over an optical assembly 410 contained within the raised cartridge mount 150. The optical assembly 410 has one or more light emitting diode ("LED") 420 light sources for fluorescence excitation. The LEDs 420 are mounted off axis and at an angle (e.g., at 65 degrees of arc) and positioned such that their light is projected into the protruding nub 241 of the polymer partitioning element 240. The angle is chosen so that the light propagates through the protruding nub 241 to illuminate its entire length. The angle and position are also set to reduce the intensity of excitation light from the LEDs 420 that is directly reflected into the detection optics of the assembly 410. Fluorescence from the partitioning element 240 follows an optical path 480 that passes through the window 430, lenses 440, fiber optic connector 450, optical fiber 460, and to an optical detector (e.g., a charged coupled device ("CCD") based spectrometer) 470 of the optical system 400. The spectrometer 470 may contain additional components such as a diffraction grating which may be required for fluorescence detection. In one embodiment, two LEDs 420 are used in the assembly 410 to provide more excitation light, and therefore fluorescence signal, than provided by one LED 420. The lenses 440 are used to collect fluorescence from the partitioning element 240 and couple it to the optical fiber 460 for transmission to the detector 470.

According to one embodiment, a single detector 470 may be used to monitor several (e.g., sixteen) optical assemblies 410 by optically combining or bundling 465 the optical fibers 460 from each assembly 410 using a single fiber optic connector 466 at or leading to the detector 470.

Figure 20:
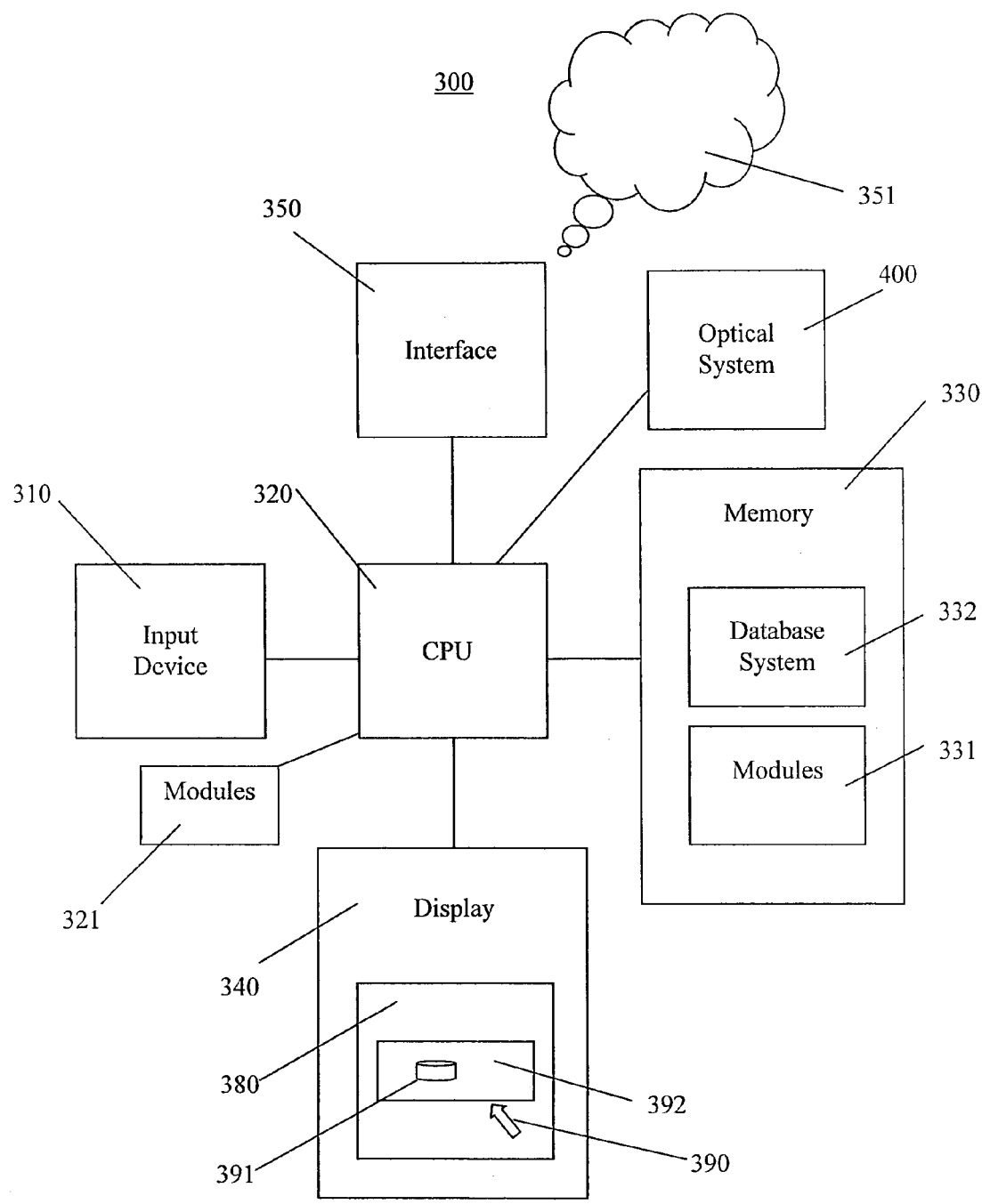
FIG. 20 is a block diagram illustrating a data processing system of the test system in accordance with an embodiment of the invention.

FIG. 20 is a block diagram illustrating a data processing system 300 of the test system 100 in accordance with an embodiment of the invention.

The optical system 400 is coupled to a data processing system 300 for analyzing data from the optical system 400 and for presenting test results to and for receiving commands from a user of the test system 100 via a graphical user interface ("GUI") 380 displayed on a display 340 of the test system 100. The GUI 380 and test system 100 allow for the multiplexing detection of biological molecules in samples in several (e.g., 16) cartridges 200 using one detector 470. This may be performed, for example, by selectively illuminating only the LEDs 420 associated with a particular fiber 460 of the bundled fibers 465.

According to one embodiment, the data processing system 300 is suitable for controlling the test system 100 in conjunction with a GUI 380, as described below. The data processing system 300 may be a client and/or server in a client/server system. For example, the data processing system 300 may be a server system or a personal computer ("PC") system. The data processing system 300 includes an input device 310, a central processing unit ("CPU") 320, memory 330, a display 340, and an interface device 350. The input device 310 may include a keyboard, a mouse, a trackball, a touch sensitive surface or screen, or a similar device. The display 340 may include a computer screen, television screen, display screen, terminal device, a touch sensitive display surface or screen, or a hardcopy producing output device such as a printer or plotter. The memory 330 may include a variety of storage devices including internal memory and external mass storage typically arranged in a hierarchy of storage as understood by those skilled in the art. For example, the memory 330 may include databases, random access memory ("RAM"), read-only memory ("ROM"), flash memory, and/or disk devices. The interface device 350 may include one or more network connections. The data processing system 300 may be adapted for communicating with other data processing systems (e.g., similar to data processing system 300) over a network 351 via the interface device 350. For example, the interface device 350 may include an interface to a network 351 such as the Internet and/or another wired or wireless network (e.g., a wireless local area network ("WLAN"), a cellular telephone network, etc.). Thus, the data processing system 300 may be linked to other data processing systems by the network 351. The CPU 320 may include or be operatively coupled to dedicated coprocessors, memory devices, or other hardware modules 321. The CPU 320 is operatively coupled to the memory 330 which stores an operating system (e.g., 331) for general management of the system 300. The CPU 320 is operatively coupled to the input device 310 for receiving user commands or queries and for displaying the results of these commands or queries to the user on the display 340. Commands and queries may also be received via the interface device 350 and results may be transmitted via the interface device 350. The data processing system 300 may include a database system 332 (or store) for storing data and programming information. The database system 332 may include a database management system and a database and may be stored in the memory 330 of the data processing system 300. In general, the data processing system 300 has stored therein data representing sequences of instructions which when executed cause the method described herein to be performed. Of course, the data processing system 300 may contain additional software and hardware a description of which is not necessary for understanding the invention.

Thus, the data processing system 300 includes computer executable programmed instructions for directing the system 300 to implement the embodiments of the present invention. The programmed instructions may be embodied in one or more hardware modules 321 or software modules 331 resident in the memory 330 of the data processing system 300 or elsewhere (e.g., 320). Alternatively, the programmed instructions may be embodied on a computer readable medium (or product) (e.g., a compact disk ("CD"), a floppy disk, etc.) which may be used for transporting the programmed instructions to the memory 330 of the data processing system 300. Alternatively, the programmed instructions may be embedded in a computer-readable signal or signal-bearing medium (or product) that is uploaded to a network 351 by a vendor or supplier of the programmed instructions, and this signal or signal-bearing medium may be downloaded through an interface (e.g., 350) to the data processing system 300 from the network 351 by end users or potential buyers.

A user may interact with the data processing system 300 and its hardware and software modules 321, 331 using a graphical user interface ("GUI") 380. The GUI 380 may be used for controlling, monitoring, managing, and accessing the data processing system 300 and test system 100. GUIs are supported by common operating systems and provide a display format which enables a user to choose commands, execute application programs, manage computer files, and perform other functions by selecting pictorial representations known as icons, or items from a menu through use of an input device 310 such as a mouse or touch screen. In general, a GUI is used to convey information to and receive commands from users and generally includes a variety of GUI objects or controls, including icons, toolbars, drop-down menus, text, dialog boxes, buttons, and the like. A user typically interacts with a GUI 380 presented on a display 340 by using an input device (e.g., a mouse or touchscreen) 310 to position a pointer or cursor 390 over an object (e.g., an icon) 391 and by "clicking" on the object 391. Typically, a GUI based system presents application, system status, and other information to the user in one or more "windows" appearing on the display 340. A window 392 is a more or less rectangular area within the display 340 in which a user may view an application or a document. Such a window 392 may be open, closed, displayed full screen, reduced to an icon, increased or reduced in size, or moved to different areas of the display 340. Multiple windows may be displayed simultaneously, such as: windows included within other windows, windows overlapping other windows, or windows tiled within the display area.

Figure 21:
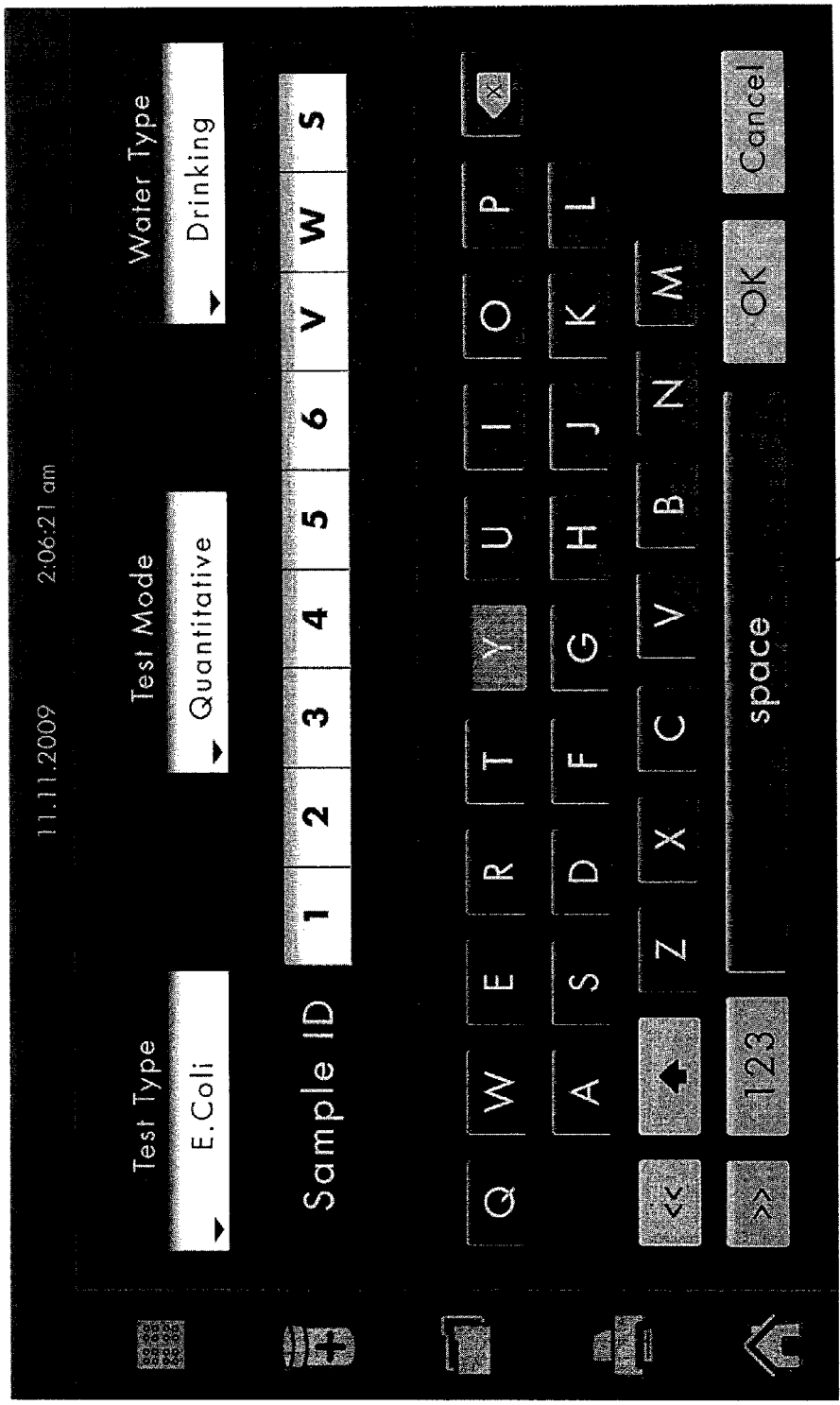
FIG. 21 is a screen capture illustrating a input screen of a graphical user interface ("GUI") of the test system in accordance with an embodiment of the invention.
Figure 22:
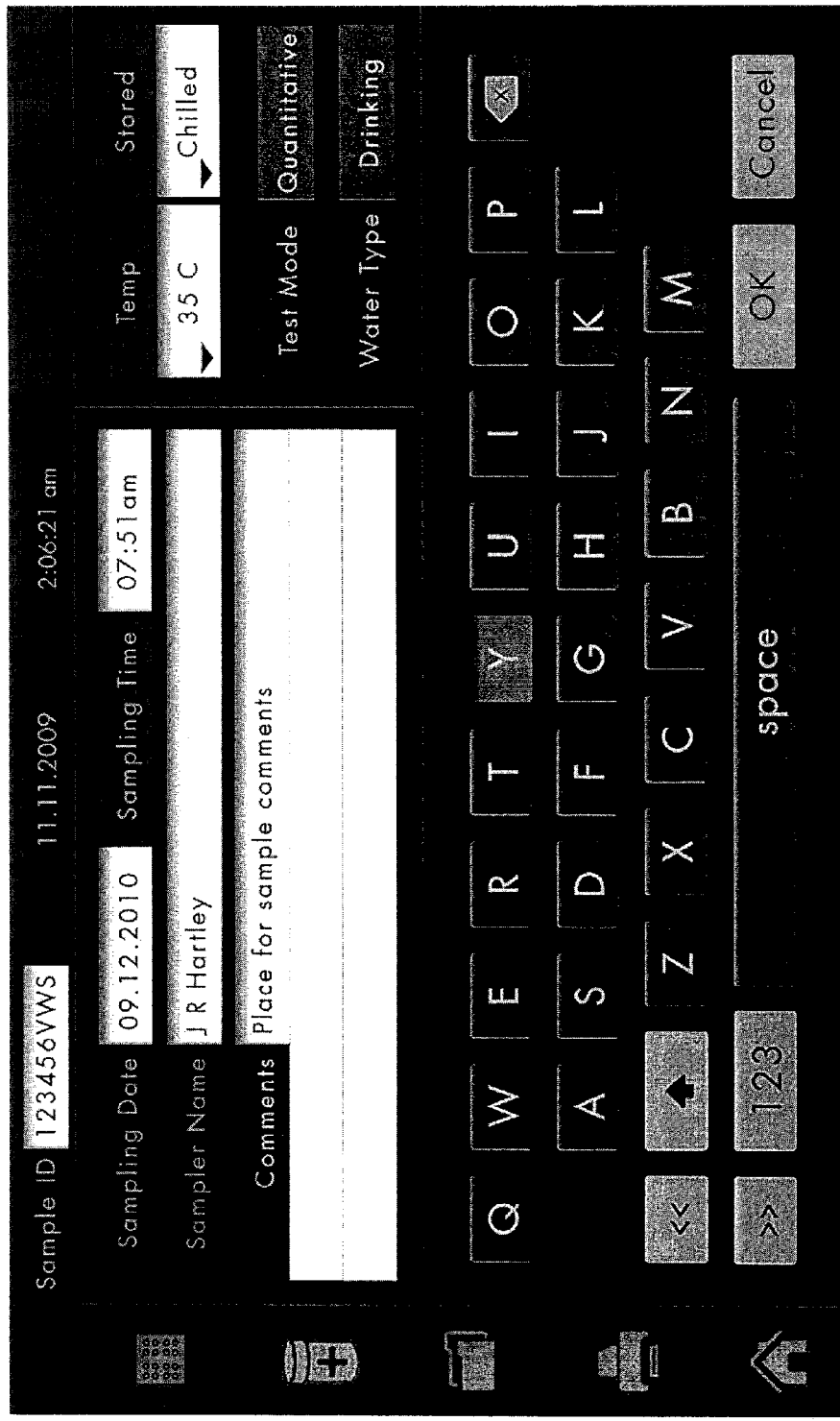
FIG. 22 is a screen capture illustrating a second input screen of a GUI of the test system in accordance with an embodiment of the invention.
Figure 23:
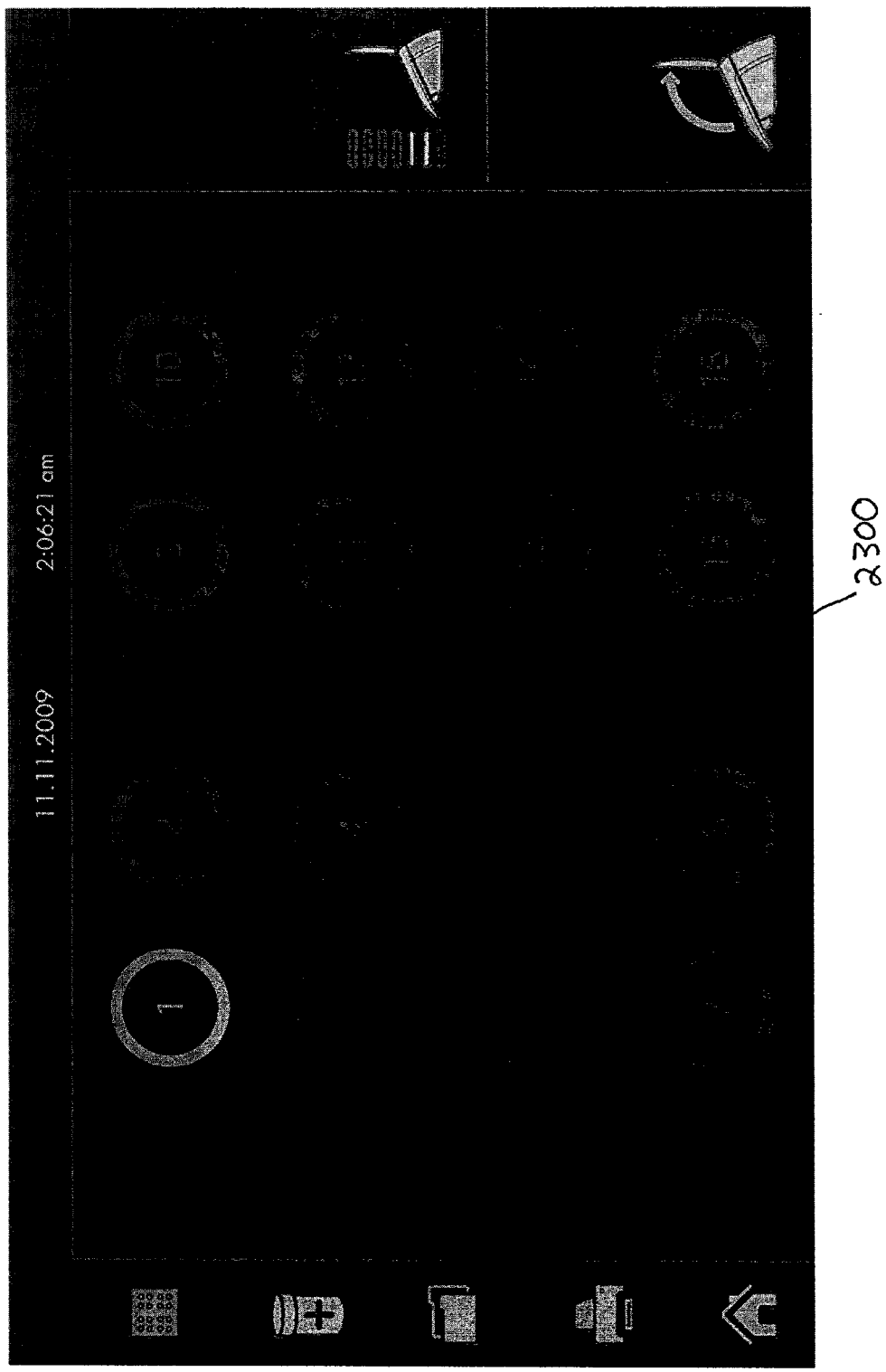
FIGS. 23 and 24 are screen captures illustrating test status screens of a GUI of the test system in accordance with an embodiment of the invention.
Figure 24:
Figure 25:
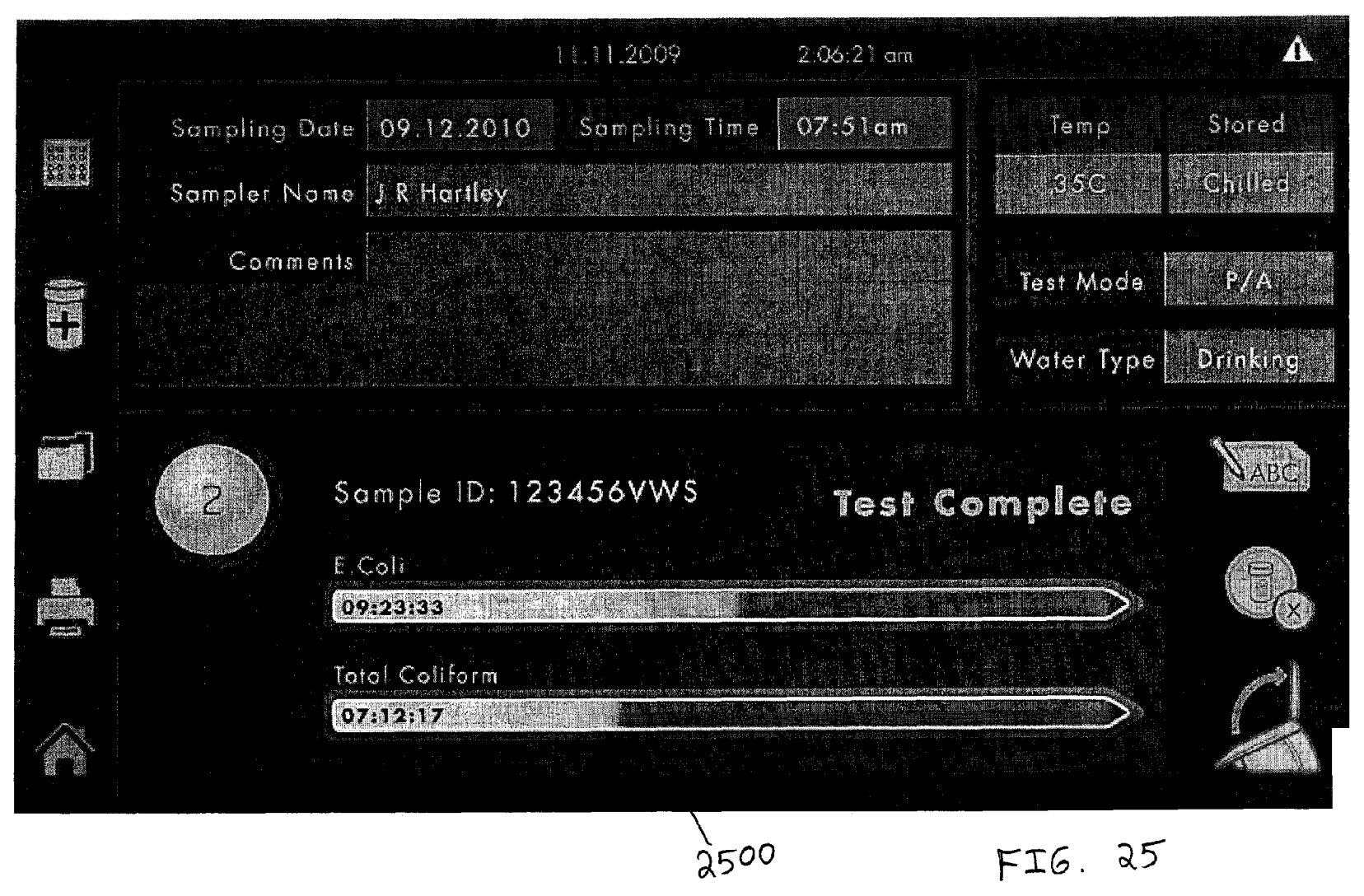
Figure 26:
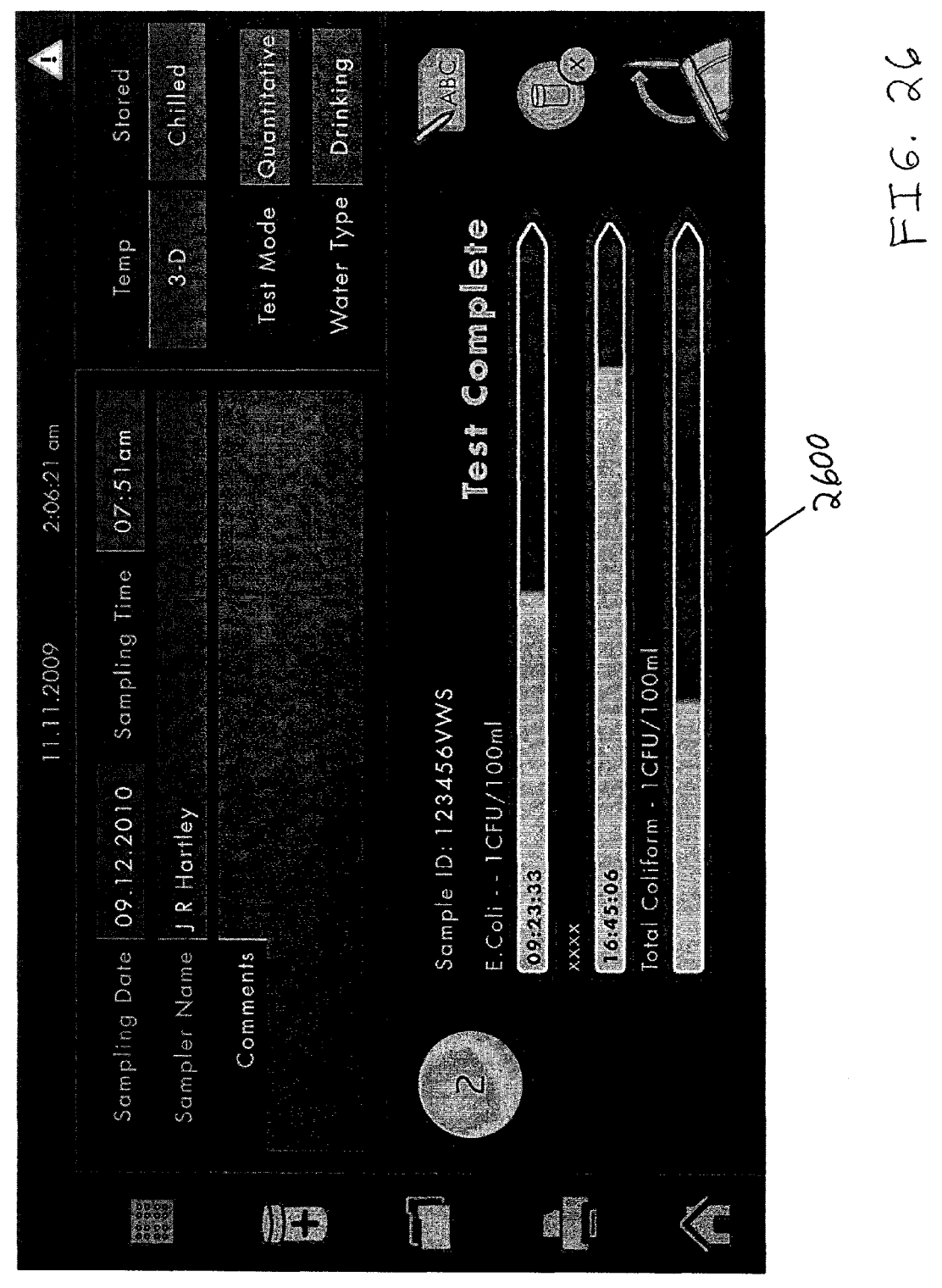
Figure 27:
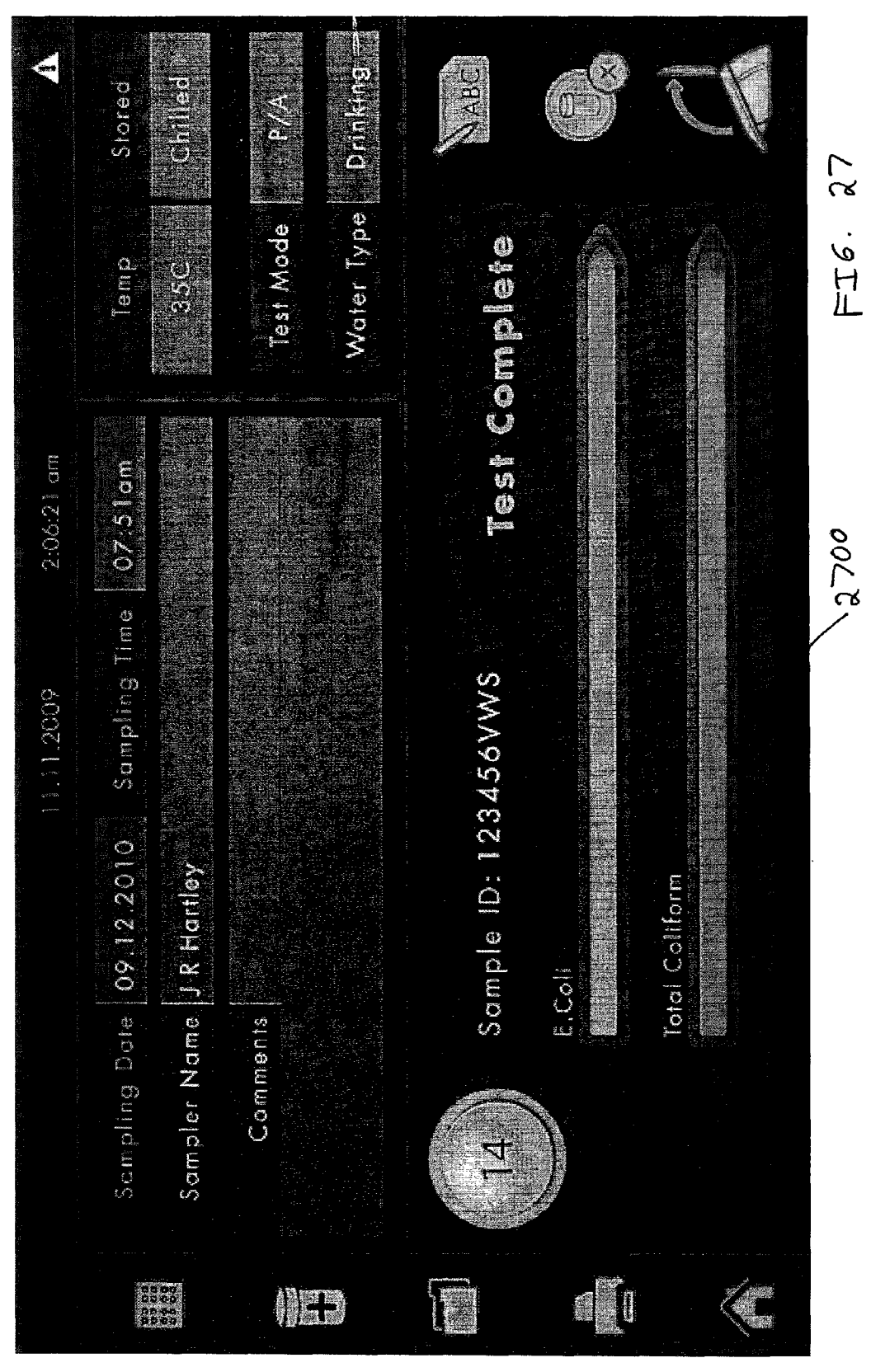
Figure 28:
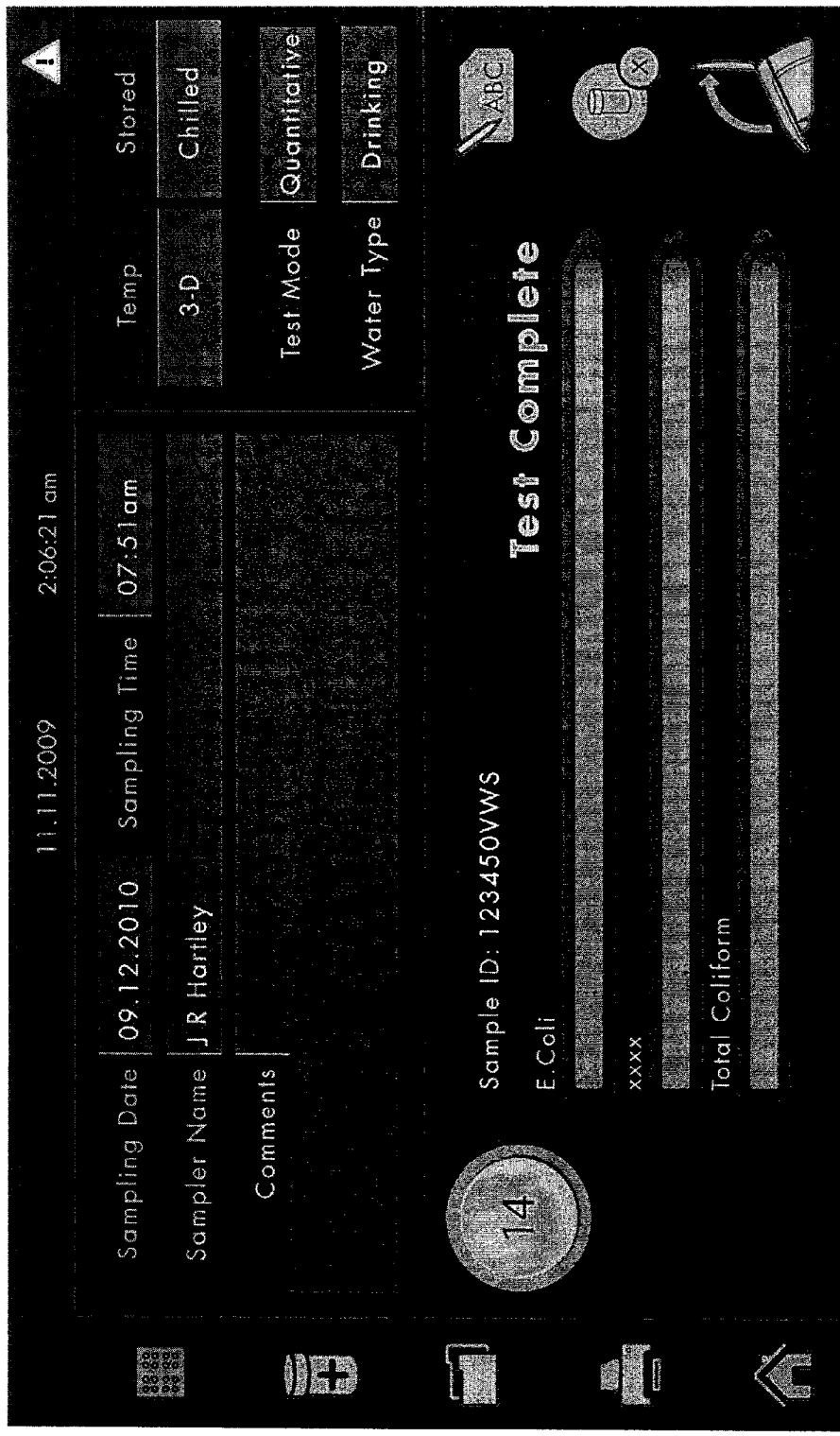
Figure 29:
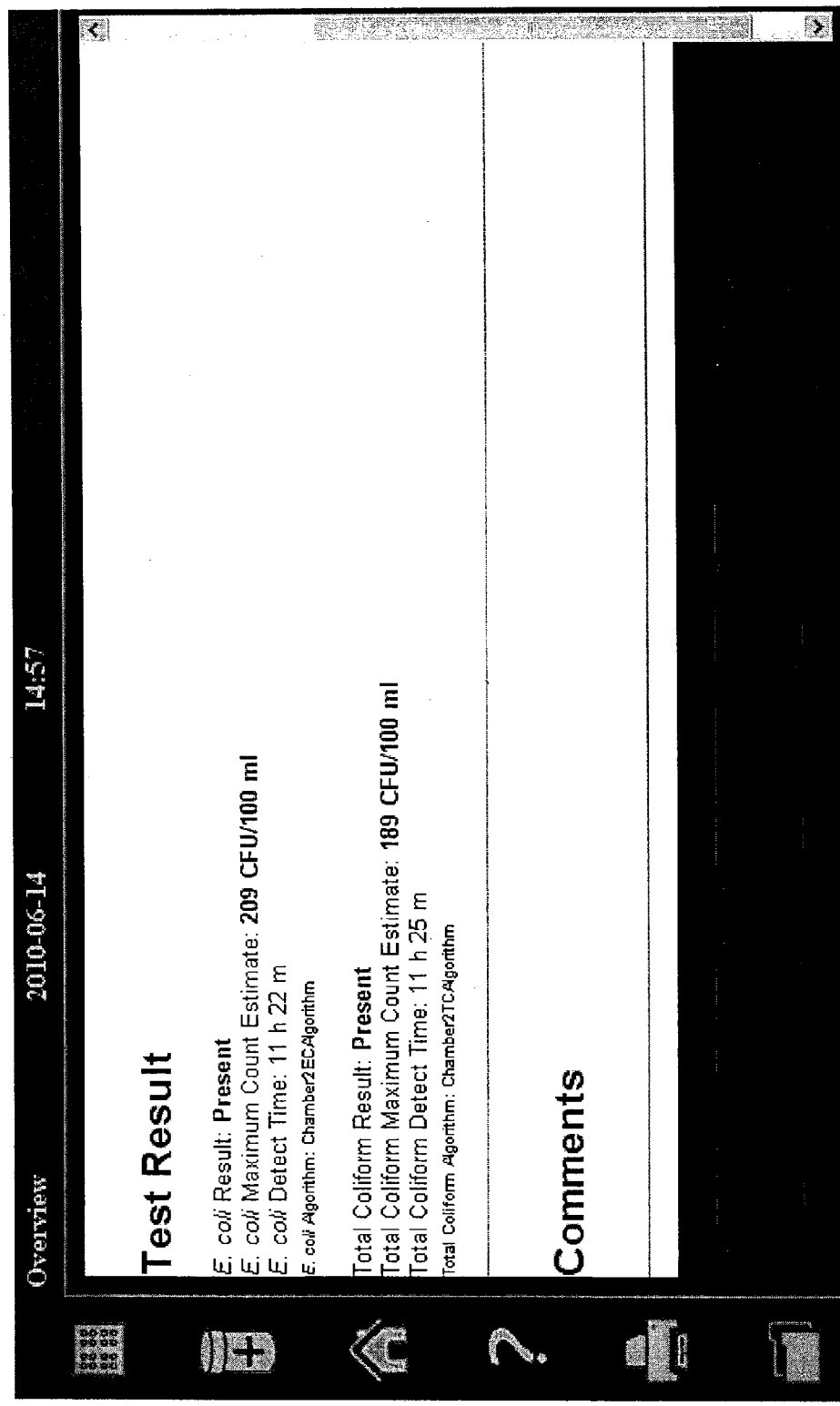
FIG. 29 is a screen capture illustrating an alternate test result screen of a GUI of the test system in accordance with an embodiment of the invention.

FIG. 21 is a screen capture illustrating an input screen 2100 of a graphical user interface ("GUI") 380 of the test system 100 in accordance with an embodiment of the invention. FIG. 22 is a screen capture illustrating a second input screen 2200 of a GUI 380 of the test system 100 in accordance with an embodiment of the invention. FIGS. 23 and 24 are screen captures illustrating test status screens 2300, 2400 of a GUI 380 of the test system 100 in accordance with an embodiment of the invention. FIGS. 25 and 26 are screen captures illustrating positive test result screens 2500, 2600 of a GUI 380 of the test system 100 in accordance with an embodiment of the invention. FIGS. 27 and 28 are screen captures illustrating negative test result screens 2700, 2800 of a GUI 380 of the test system 100 in accordance with an embodiment of the invention. And, FIG. 29 is a screen capture illustrating an alternate test result screen 2900 of a GUI 380 of the test system 100 in accordance with an embodiment of the invention.

The screen captures of FIGS. 21-29 show various input, status, and reporting screen presentations associated with the GUI 380 of the data processing system 300 of the test system 100.

Thus, according to one embodiment, there is provided a method and system 100 for the reliable and rapid detection of biological molecules associated with enzyme activity. The invention is applicable to the detection of biological molecules associated with enzyme activity of biological contaminants, such as microorganisms. One practical application of the invention therefore relates to the detection of biological contaminants in samples such as water and food, where rapid detection is critical to preventing the spread of contamination and infection of individuals through consumption of contaminated water or food. Another practical application of the invention is use in assays, such as enzyme-linked immunosorbent assay ("ELISA"), for determination of enzyme labels.

In particular, the invention provides for reliable and rapid detection of enzyme activity. According to the invention, target enzyme activity is detected by providing to an enzyme a substrate comprising a fluorophore, and selectively detecting fluorescence of a fluorescent product of the enzyme-substrate reaction at a very low product concentration. Alternatively, target enzyme activity is detected by providing to an enzyme a substrate comprising a fluorophore, and selectively detecting fluorescence of the substrate and its rate of decrease as the enzyme-substrate reaction proceeds. Selective detection of the fluorescent product or substrate is achieved by providing an optical system 400 and a partitioning element 240, wherein one of the product or substrate 210 is partitioned into the partitioning element 240. The optical system 400 includes suitable optical hardware for detecting fluorescence of the product or substrate partitioned into the partitioning element 240.

The ability to detect a product of the enzyme-substrate interaction at a very low product concentration or a minute change in substrate concentration translates into rapid detection because of the short time required to produce only a small amount of the product, or remove a small amount of substrate. In embodiments in which the presence of microorganisms is detected, therefore, only a small number of microorganisms, and hence a short incubation period, is required for detection. While the invention is described primarily with respect to the detection of enzyme-substrate product, it will be understood that the invention is equally applicable to the detection of substrate.

Detection of enzyme activity according to the invention can be carried out in any medium where target enzymes are active, and which is sufficiently fluid to allow for partitioning of a molecule of interest, such as a product of the enzyme-substrate reaction, into the partitioning element 240. Suitable media are aqueous, and may be fluids (e.g., liquids) or semi-solids (e.g., biological tissues, gels). Generally, the invention is used to detect a target enzyme in a sample, such as, for example, water, food, biological samples such as tissues and bodily fluids, and soil. Analysis of some samples, such as certain food, biological, and soil samples, requires that the sample be combined with a suitable medium.

According to one embodiment, there is provided a method of detecting biological molecules associated with enzyme activity in a sample. The method comprises combining a target enzyme or a biological contaminant associated with the target enzyme and a substrate, irradiating the combination with excitation light (i.e., light of a wavelength which produces fluorescence in either or both the substrate and product), and selectively detecting fluorescence of either the substrate or any product of the enzyme-substrate reaction when partitioned into the partitioning element. Preferably, fluorescence of a fluorescent product of the enzyme-substrate reaction is detected. Where the sample is not substantially a liquid or semi-liquid (e.g., a gel), it is preferable that the substrate and sample are combined in a solution. Suitable solutions include any solution which can support and/or promote enzyme activity. Where cells are employed, a suitable solution may be, for example, an appropriate medium (i.e., "broth") selected to support and promote growth of the cells under investigation. For cells and most enzymes, such solutions are aqueous. The product of the enzyme-substrate reaction can be, for example, a free fluorescent (dye) molecule, the fluorescence of which is detected.

According to one embodiment, fluorescence is detected by an optical system 400 which distinguishes between the product and the substrate, such that only fluorescence of the product or the substrate is detected. In particular, fluorescence of either the product or the substrate is detected by providing a partitioning element 240 that allows for partitioning of substantially only one of the product or the substrate therein. When coupled to a suitable device for measuring fluorescence (i.e., light), such as, for example, a spectrometer or a filter photometer (e.g., 470) included within the optical system 400, the partitioning element 240 and optical system 400 produce a signal having a magnitude which varies predictably (e.g., linearly) with the intensity of the fluorescence, which is a function of the product or substrate concentration. According to one embodiment, the combination of substrate, product, and partitioning element 240 is chosen such that the substrate is not detected and the product is detected at the lowest possible concentration.

It will be appreciated that the invention can be applied to detection of activity of any enzyme, provided that (1) a substrate for such target enzyme can be conjugated with a fluorophore, (2) the target enzyme-substrate reaction produces a fluorescent product, and (3) the fluorescent product can be selectively detected with a partitioning element 240 and optical system 400 of the invention. For enzymes which cleave chemical bonds, the substrate must contain a moiety which binds to the enzyme, and be conjugated to the fluorescent product through a bond which the enzyme will cleave. For other enzyme reactions, such as some peroxidase reactions in which there is only chemical conversion of the substrate to give the product, suitable substrates are those which provide for the product being partitioned into the partitioning element 240.

It will be appreciated that the invention can be used to detect the presence of more than one enzyme, which may correspond to more than one species or strain of microorganism, simultaneously. This requires the use of a substrate suitable for each enzyme under consideration. If the fluorescent products of each different enzyme-substrate reaction fluoresce at different wavelengths, then activity of each enzyme under consideration can be detected. Alternatively, if the fluorescent products of each different enzyme-substrate reaction fluoresce at the same wavelength, then activity of at least one of the enzymes can be detected.

According to one embodiment, there is provided a partitioning element 240 and an optical system 400 for selectively-detecting fluorescent molecules. In particular, the partitioning element 240 provides for partitioning of molecules into the element, wherein detected fluorescence is predominantly that of molecules partitioned into the element. Such partitioning of molecules is achieved by disposing in a test cartridge 200 a partitioning element 240 and detecting fluorescence with an optical system 400. The partitioning element 240 allows only a molecule of interest to be partitioned therein.

For example, to detect enzyme activity using a fluorogenic substrate and fluorescent enzyme-substrate product, the invention provides a partitioning element 240 which allows for only the substrate or product molecules to partition therein, such that fluorescence of either the substrate or the product is detected by the optical system 400. Thus, it matters not whether both the substrate and the product are fluorescent, as the optical system 400 detects fluorescence from only one of the two. Enzyme activity can then be determined by measuring the rate of disappearance of substrate fluorescence, or the rate of appearance of product fluorescence. According to one embodiment, product molecules are partitioned into the partitioning element 240, and enzyme activity is determined by measuring the rate of appearance of product fluorescence. As noted above, detection of enzyme activity according to the invention can be carried out in any medium where target enzymes are active. Generally, such media are aqueous, and they may be fluids (e.g., liquids) or semi-solids (e.g., biological tissues, gels).

According to one embodiment, there is provided a test system 100 that employs a test cartridge 200 with an integrated partitioning element 240 that is capable of delivering presence/absence and bacteriological count estimation for a wide variety of pathogens, including, but not limited to, *E. coli* and total coliform bacteria. According to one embodiment, the test cartridge 200 is a disposable, single use cartridge. The test system 100 uses a test cartridge 200 with integral partitioning element 240 in which individual samples are contained. The optical system 400 of the test system 100 is external to the test cartridge 200. The partitioning element 240 does not contact multiple samples thereby reducing a potential source of cross-contamination between samples. This reduces the need to clean elements of the optical system 400 between tests. According to one embodiment, the test system 100 includes a calibration method based on multiple fluorophores that provides continuous optical path integrity monitoring and self-calibration. The test system 100 optionally provides for performing multiple tests for different pathogens.

The test cartridge 200 incorporates elements necessary to conduct a bacteriological test for a specific target pathogen, including but not limited to *E. coli* and total coliform bacteria. The test cartridge 200 includes a sealable casing or body enclosing a sterile interior that can be manipulated by simple mechanics in the test system 100. The partitioning element 240 and a test medium in either solid, powdered, or liquid form are contained within the body of the test cartridge 200. The test medium includes one or more substrate materials (e.g., 210), for example, glucuronide or galactoside substrate materials, each substrate material including a target fluorophore. The test medium may also include an additional (or second) fluorophore (i.e., a calibration fluorophore) that dissolves in an aqueous environment to provide a baseline optical signal for calibration and monitoring of optical signal path integrity, and a growth medium to support growth of the target organism(s). The test medium may optionally include: sodium thiosulfate to remove free chlorine from a water sample; antibiotic to inhibit growth of non-target microorganisms; and, a compound that reacts in the presence of the target pathogen to produce a colour change as visual confirmation of the presence of the target pathogen in the sample.

The test system 100 includes an optical system 400 for detecting the fluorophore of interest (e.g., a fluorophore produced upon degradation of the substrate by target enzyme action). The optical system 400 together with the partitioning element 240 function on the principles described above. Thus, the optical system 400 includes a light source 420, such as a UV light source or LEDs, for irradiating the partitioning element 240 of the test cartridge 200, and an optical detector such as a CCD detector 470, for detecting fluorescence of the target fluorophore partitioned into the partitioning element 240. The test system 100 may also include optics for irradiating and detecting the calibration fluorophore, mentioned above, to provide a baseline optical signal for calibration and/or monitoring of the optical signal path integrity. In such embodiment, fluorescence produced by the target and calibration fluorophores must be differentiated and detected. Thus, for example, the optical path 480 for detecting fluorescence emitted from the partitioning element 240 may include a beam splitter and mirror that splits the optical path 480 into two channels. Each channel may be filtered using an optical filter at the wavelength of the fluorophore of interest (i.e., the target and calibration fluorophores) and the filtered optical signals may be subsequently detected.

According to one embodiment, the test system 100 includes a data processing system 300 to allow users to control its operation. The data processing system 300 may include acquisition/processing/display devices and an interface (e.g., to the Internet, etc.) to allow the system 100 to be networked to an external supervisory control and data acquisition ("SCADA") system.

Thus, according to one embodiment, there is provided a system 100 for detecting presence of an organism having an enzyme in a sample, comprising: a cartridge 200 for containing the sample and a substrate 210 such that the enzyme can react with the substrate to produce a biological molecule; a partitioning element 240 mounted in a recess 250 in a base 220 of the cartridge 200, the partitioning element 240 allowing partitioning of the biological molecule thereinto; a light source 420 for irradiating the biological molecule partitioned into the partitioning element 240; and, a detector 470 for detecting fluorescence of the biological molecule partitioned into the partitioning element 240, the detected fluorescence being indicative of presence of the organism in the sample; wherein the light source 420 is in a raised cartridge mount 150 of the system 100 that mates with the recess 250 in the base 220 of the cartridge 200. The recess 250 in the base 220 of the cartridge 200 prevents contact of the optical coupling interface (e.g., light source 420, etc.) with surfaces or other sources of debris or contamination during handling of the sample.

The system 100 may further include a test chamber 130 for receiving the cartridge. The test chamber 130 may be an incubator having a heating system associated therewith. The raised cartridge mount 150 may be positioned at an angle within the system 100 to minimize residue build-up on optical components (e.g., 430, 440, 450) and avoid contact of the sample with a lid 230 of the cartridge 200. The angle may be about 25 degrees. The raised cartridge mount 150 may include a sensor 160 for detecting whether the cartridge 200 is present. The light source 420 may be a light emitting diode ("LED"). The LED 420 may be mounted at an angle to reduce direct reflection of light from the light source 420 off of the base 220 of the cartridge 200 toward optical components (e.g., 430, 440, 450) of the system 100 and to optimize detection of fluorescence of the biological molecule partitioned into the partitioning element 240. The angle may be about 65 degrees. And, the recess 250 may have a depth that is selected to reduce contact of the partitioning element 240 with contaminants. Note that the sample may be in a liquid phase and/or a solid phase.

While aspects of this invention may be discussed as a method, a person of ordinary skill in the art will understand that the apparatus discussed above with reference to a data processing system 300 may be programmed to enable the practice of the method of the invention. Moreover, an article of manufacture for use with a data processing system 300, such as a pre-recorded storage device or other similar computer readable medium including program instructions recorded thereon, may direct the data processing system 300 to facilitate the practice of the method of the invention. It is understood that such apparatus and articles of manufacture also come within the scope of the invention.

In particular, the sequences of instructions which when executed cause the method described herein to be performed by the data processing system 300 can be contained in a data carrier product according to one embodiment of the invention. This data carrier product can be loaded into and run by the data processing system 300. In addition, the sequences of instructions which when executed cause the method described herein to be performed by the data processing system 300 can be contained in a computer software product according to one embodiment of the invention. This computer software product can be loaded into and run by the data processing system 300. Moreover, the sequences of instructions which when executed cause the method described herein to be performed by the data processing system 300 can be contained in an integrated circuit product (e.g., a hardware module or modules 321) which may include a coprocessor or memory according to one embodiment of the invention. This integrated circuit product can be installed in the data processing system 300.

The embodiments of the invention described above are intended to be exemplary only. Those skilled in this art will understand that various modifications of detail may be made to these embodiments, all of which come within the scope of the invention.

What is claimed is:

1. An apparatus for detecting presence of an organism in a sample, comprising:
    a removable cartridge that contains the sample and a substrate such that an enzyme of the organism can react with the substrate to produce a biological molecule, wherein the cartridge has a base including an inwardly-projecting recess;
    a partitioning element associated with the recess, wherein the partitioning element has a protruding portion that projects substantially axially into the cartridge;
    a test chamber that receives the cartridge and maintains the cartridge in a selected position, wherein the test chamber includes a raised cartridge mount that engages the recess in the cartridge and is in optical communication with the partitioning element;
    an excitation light source disposed in the raised cartridge mount in an orientation relative to the axially projecting protruding portion, wherein the orientation is selected such that excitation light propagates into the protruding portion substantially along its entire length, and such that reflection of excitation light is reduced; and,
    a detector that detects fluorescence of the biological molecule partitioned into the partitioning element, the detected fluorescence being indicative of presence of the organism in the sample.

2. The apparatus of claim 1, wherein the test chamber comprises an incubator having a heating system associated therewith.

3. The apparatus of claim 1, wherein the selected position minimizes residue build-up on the protruding portion of the partitioning element and avoids contact of the sample with a lid of the cartridge.

4. The apparatus of claim 3, wherein the selected position comprises the protruding portion projecting axially at an angle of about 25 degrees relative to horizontal.

5. The apparatus of claim 1, wherein the raised cartridge mount includes a sensor for detecting whether the cartridge is present.

6. The apparatus of claim 1, wherein the excitation light source is a light emitting diode (LED).

7. The apparatus of claim 1, wherein the orientation of the excitation light source is an angle of about 32.5 degrees relative to the axially projecting protruding portion.

* * * * *